US008445275B2

(12) United States Patent
Hochrein et al.

(10) Patent No.: US 8,445,275 B2
(45) Date of Patent: *May 21, 2013

(54) INDUCTION OF DENDRITIC CELL DEVELOPMENT WITH MACROPHAGE-COLONY STIMULATING FACTOR (M-CSF)

(75) Inventors: Hubertus Hochrein, Munich (DE); Meredith O'Keeffe, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 533 days.

This patent is subject to a terminal disclaimer.

(21) Appl. No.: 12/596,175

(22) PCT Filed: Apr. 25, 2008

(86) PCT No.: PCT/EP2008/003366
§ 371 (c)(1),
(2), (4) Date: Oct. 16, 2009

(87) PCT Pub. No.: WO2008/131926
PCT Pub. Date: Nov. 6, 2008

(65) Prior Publication Data
US 2010/0167332 A1 Jul. 1, 2010

Related U.S. Application Data

(63) Continuation-in-part of application No. 11/790,798, filed on Apr. 27, 2007, now Pat. No. 8,053,234.

(30) Foreign Application Priority Data

Apr. 30, 2007 (EP) .................................. 07008785

(51) Int. Cl.
*C12N 5/071* (2010.01)
*C12N 5/00* (2006.01)
*C12N 5/02* (2006.01)
*A01N 63/00* (2006.01)

(52) U.S. Cl.
USPC ......................... 435/372; 435/377; 424/93.71

(58) Field of Classification Search
None
See application file for complete search history.

(56) References Cited

U.S. PATENT DOCUMENTS

| 7,198,948 B2 | 4/2007 | Steinman |
| 2008/0267994 A1 | 10/2008 | Hoichrein |
| 2009/0148405 A1 | 6/2009 | Hochrein et al. |

FOREIGN PATENT DOCUMENTS

| EP | 0 326 149 A2 | 8/1989 |
| WO | WO2004/020613 A1 | 3/2004 |

OTHER PUBLICATIONS

Nassar et al., 1994, Antimicr. Agents. CHem. vol. 38: 2162-2164.*
Oliveira et al., 2003, J. Leuk. Biol. vol. 74: 857-867.*
Dilioglou et al., 2003, Exp. Mol. Path. vol. 75: 217-227.*
Kim et al., Macrophage Colony-Stimulating Factor Can Modulate Immune Responses and Attrct Dendritic Cells in Vivo, Human Gene Therapy 11:305-311 (2000).
Misawa et al., Administration of macrophage colony-stimulating factor mobilized both CD11b+CD11c cells and NK1.1+ cells into peripheral cells, International Immunopharmacology 4:791-803 (2004).
Fancke et al., M-CSF: a novel pasmacytoid and conventional dendritic cell poietin, Blood 111:150-159 (2008) (prepublished online Oct. 4, 2007).
Lin et al., Discovery of a Cytokine and Its Receptor by Functional Screening of the Extracellular Proteome, Science 320:807-811 (2008).
Di Nicola et al., Boosting T Cell-Mediated Immunity to Tyrosinase by Vaccinia Virus-Transduced, CD34+-Derived Dendritic Cell Vaccination: A Phase I Trial in Metastatic Melanoma, Clinical Cancer Research, vol. 10, 5381-5390, Aug. 15, 2004.
Bernhard et al., Generation of Immunostimulatory Dendritic Cells from Human CD34+ Hematopoietic Progenitor Cells of the Bone Marrow and peripheral Blood, Cancer Research 55:1099-1104 (1995).
Koya et al., Making Dendritic Cells from the Inside Out: Lentiviral Vector-Mediated Gene Delivery of Granulocyte-Macrophage Colony-Stimulating Factor and Interleukin 4 into CD14+ Monocytes Generates Dendritic Cells In Vitro, Human Gene Therapy 15:733-748 (2004).
Zhang et al., Macrophage colony-stimulating factor expression in retrovirally transduced cells is dependent upon both the adherence status of the target cells and its 5' flanking untranslated region, BBRC 330:1275-1284 (2005).
Chen et al., Thrombopoietin cooperates with FLT3-ligand in the generation of plasmacytoid dendritic cell precursors from human hematopoietic progenitors, Blood 103:2547-2553 (2004).
Bangert et al., Immunopathologic Features of Allergic Contact Dermatitis in Humans: Participation of Plasmacytoid Dendritic Cells in the Pathogenesis of the Disease? J Invest Dermatol 121:1409-1418 (2003).

(Continued)

*Primary Examiner* — Amy Juedes
(74) *Attorney, Agent, or Firm* — Law Office of Salvatore Arrigo and Scott Lee, LLP

(57) ABSTRACT

A method of inducing dendritic cell (DC) development by administering Macrophage-Colony Stimulating Factor (M-CSF) is provided. M-CSF induces DCs to differentiate into Subtypes, for example plasmacytoid DCs and conventional DCs. Said differentiation is independent of Fms-like-Tyrosine-Kinase 3-Ligand (FL) and/or Granulocyte-Macrophage-Colony Stimulating Factor (GM-CSF). Induction with M-CSF can be achieved in vitro from hematopoietic precursors, such as bone marrow cells, or in vivo. In vitro, M-CSF-derived DCs can be used to produce cytokines and to stimulate other immune response cells. M-CSF can also be used to induce precursor cells removed from an animal to develop into DCs. In addition, these isolated DCs can be exposed to antigens to stimulate a specific immune response when reintroduced into the animal. Treatments for Cancers, such as Acute Myeloid Leukemia, and autoimmune diseases such as Systemic Lupus Erythematosus, are also provided in the invention.

21 Claims, 8 Drawing Sheets

OTHER PUBLICATIONS

Wood et al., Human Dendritic Cells and Macrophages: In Situ Immunophenotypic Definition of Subsets That Exhibit Specfic Morphologic and Microenvironmental Characteristics, Am J Pathol 119:73-82 (1985).
Grouard et al., The Enigmatic Plasmacytoid T Cells Develop into Dendritic Cells with Interleukin (IL)-3 and CD40-Ligand, J. Exp. Med. vol. 185, No. 6, Mar. 17, 1997 1101-1111.
MacDonald et al., Characterization of human blood dendritic cell subsets, Blood 100:4512-4520 (2002).
Nikolic et al., Developmental stages of myeloid dendritic cells in mouse bone marrow, International Immunology 15:515-524 (2003).
Xu et al., Improved Immunostimulatory Function of Bone Maorrow Derived Macrophages Transduced with the Granulocyte-Macrophage Colony Stimulating Factor Gene, Cancer Biotherapy & Radiopharmaceuticals 12:27-36 (1997).
Tadokoro et al., Bone marrow-derived macrophages grown in GM-CSF or M-CSF differ in their ability to produce IL-12 and to induce IFN-gamma production after stimulation with Trypanosoma Cruzi antigens, Immunology Letters 77:31-38 (2001).
Yamamoto-Yamaguchi et al., Effect of mouse interferon on growth and differentiation of mouse bone marrow cells stimulated by two different types of colony-stimulating factor, Blood 62:597-601 (1983).
Advani AS. 2005. FLT3 and acute myelogenous leukemia: biology, clinical significance and therapeutic applications. Curr Pharm Des. 11:3449-57.
Barbaroux Jean-Baptiste et al. 2006. Tumor necrosis factor-alpha- and IL-4-independent development of Langerhans cell-like dendritic cells from M-CSF-conditioned precursors. The Journal of Investigative Dermatology, vol. 126, No. 1, 114-120.
Bartocci,A., D.S.Mastrogiannis, G.Migliorati, R.J.Stockert, A.W. Wolkoff, and E.R.Stanley. 1987. Macrophages specifically regulate the concentration of their own growth factor in the circulation. Proc. Natl. Acad. Sci. U. S. A 84:6179-6183.
Bjorck,P. 2001. Isolation and characterization of plasmacytoid dendritic cells from Flt3 ligand and granulocyte-macrophage colony-stimulating factor-treated mice. Blood 98:3520-3526.
Brasel,K., S.T.De, J.L.Smith, and C.R.Maliszewski. 2000. Generation of murine dendritic cells from flt3-ligand-supplemented bone marrow cultures. Blood 96:3029-3039.
Brawand,P., D.R.Fitzpatrick, B.W.Greenfield, K.Brasel, C.R. Maliszewski, and T.De Smedt. 2002. Murine plasmacytoid pre-dendritic cells generated from Flt3 ligand-supplemented bone marrow cultures are immature APCs. J. Immunol. 169:6711-6719.
Briard D et al. 2005. Importance of stromal determinants in the generation of dendritic and natural killer cells in the human spleen. Clinical and Experiment Immunology vol. 140, No. 2, 265-273.
Chitu,V. and E.R.Stanley. 2006. Colony-stimulating factor-1 in immunity and inflammation. Curr. Opin. Immunol 18:39-48.
Christensen and Shlomochik. 2007. Regulation of lupus-related autoantibody production and clinical disease by Toll-like receptors. Semin. Immunol. 19: 11-23.
Cremer Isabelle et al. 2002. Long-lived immature dendritic cells mediated by Trance-Rank interaction. Blood vol. 100, No. 10, 3646-3655.
D'Amico,A. and L.Wu. 2003. The early progenitors of mouse dendritic cells and plasmacytoid predendritic cells are within the bone marrow hemopoietic precursors expressing Flt3. J. Exp. Med 198:293-303.
Diebold,S.S., M.Montoya, Hunger, L.Alexopoulou, P. Roy, L.E. Haswell, A.Al Shamkhani, R. Flavell, P.Borrow, and Reis E Sousa. 2003. Viral infection switches non-plasmacytoid dendritic cells into high interferon producers. Nature 424:324-328.
Fogg et al., 2006. A Clonogenic Bone Marrow Progenitor Specific for Macrophages and Dendritic Cells. Science, 311:83-87.
Franchini,M., H.Hefti, S.Vollstedt, B.Glanzmann, M.Riesen, M.Ackermann, P.Chaplin, K.Shortman, and M.Suter. 2004. Dendritic cells from mice neonatally vaccinated with modified vaccinia virus Ankara transfer resistance against herpes simplex virus type I to naive one-week-old mice. J. Immunol. 172:6304-6312.
Gill,M.A., P.Blanco, E.Arce, V.Pascual, J.Banchereau, and A.K. Palucka. 2002. Blood dendritic cells and DC-poietins in systemic lupus erythematosus. Hum. Immunol. 63:1172-1180.
Gilliet,M., A.Boonstra, C.Paturel, S.Antonenko, X.L.Xu, G.Trinchieri, A.O'Garra, and Y.J.Liu. 2002. The development of murine plasmacytoid dendritic cell precursors is differentially regulated by FLT3-ligand and granulocyte/macrophage colony-stimulating factor. J. Exp. Med 195:953-958.
Graf C, Heidel F, Tenzer S, Radsak MP, Solem FK, Britten CM, Huber C, Fischer T, Wolfel T. 2006. A neoepitope generated by a FLT3 internal tandem duplication (FLT3-ITD) is recognized by leukemia-reactive autologous CD8+ T cells. Blood 109(7):2985-8 Prepublished online Nov. 21, 2006; DOI 10.1182/blood-2006-07-032839.
Guha-Thakurta,N. and J.A.Majde. 1997. Early induction of proinflammatory cytokine and type I interferon mRNAs following Newcastle disease virus, poly [rl:rC], or low-dose LPS challenge of the mouse 1. J Interferon Cytokine Res. 17:197-204.
Hochrein,H., B.Schlatter, M.O'Keeffe, C.Wagner, F.Schmitz, M.Schiemann, S.Bauer, M.Suter, and H.Wagner. 2004. Herpes simplex virus type-1 induces IFN-alpha production via Toll-like receptor 9-dependent and -independent pathways. Proc. Natl. Acad. Sci. U. S. A 101:11416-11421.
Hsu et al. 1996. Vaccination of Patients with B-Cell Lymphoma Using Autologous Antigen-Pulsed Dendritic Cells. Nat. Med. 2:52-58.
Hübel, et al, 2002. Therapeutic use of cytokines to modulate phagocyte function for the treatment of infections diseases: Current status of Granulocyte Colony-Stimulating Factor, Granulocyte-Macrophage Colony-Stimulating Factor, Macrophage Colony-Stimulating Factor, and Interferon-γ. J. Infect. Dis., 185: 1490-501.
Inaba,K., M.Inaba, N.Romani, H.Aya, M.Deguchi, S.Ikehara, S.Muramatsu, and R.M.Steinman. 1992. Generation of large numbers of dendritic cells from mouse bone marrow cultures supplemented with granulocyte/macrophage colony-stimulating factor. J Exp. Med. 176:1693-1702.
Ishii,K.J. and S.Akira. 2006. Innate immune recognition of, and regulation by, DNA. Trends Immunol 27:525-532.
Itoh,Y., T.Okanoue, S.Sakamoto, K.Nishioji, and K.Kashima. 1997. The effects of prednisolone and interferons on serum macrophage colony stimulating factor concentrations in chronic hepatitis B. J Hepatol. 26:244-252.
Kamps A W A et al. 1999. Role of macrophage colony-stimulating factor in the differentiation and expansion of monocytes and dendritic cells from cd34+ progenitor cells. Medical Oncology, 16(1): 46-52.
Kappelmayer J, Udvardy M, Antal-Szalmas P. 2007. Pgp and FLT3: identification and modulation of two proteins that lead to chemotherapy resistance in acute myeloid leukemia. Curr Med Chem., 14:519-30.
Karsunky,H., M.Merad, A.Cozzio, I.L.Weissman, and M.G.Manz. 2003. Flt3 ligand regulates dendritic cell development from Flt3+ lymphoid and myeloid-committed progenitors to Flt3+ dendritic cells in vivo. J Exp. Med. 198:305-313.
Kreisel,F.H., A.Blasius, D.Kreisel, M.Colonna, and M.Cella. 2006. Interferon-producing cells develop from murine CD31(high)/Ly6C(−) marrow progenitors. Cell Immunol 242:91-98.
Krug,A., S.Rothenfusser, V.Hornung, B.Jahrsdorfer, S.Blackwell, Z.K.Ballas, S.Endres, A.M.Krieg, and G.Hartmann. 2001. Identification of CpG oligonucleotide sequences with high induction of IFN-alpha/beta in plasmacytoid dendritic cells. Eur. J. Immunol. 31:2154-2163.
MacDonald,K.P., V.Rowe, A.D.Clouston, J.K.Welply, R.D.Kuns, J.L.Ferrara, R.Thomas, and G.R.Hill. 2005. Cytokine expanded myeloid precursors function as regulatory antigen-presenting cells and promote tolerance through IL-10-producing regulatory T cells. J. Immunol. 174:1841-1850.
MacDonald,K.P. et al. 2005. The colony-stimulating factor 1 receptor is expressed on dendritic cell s during differentiation and regulates their expansion. J. Immunol, vol. 175, No. 3, 1399-1405.

Maraskovsky,E., K.Brasel, M.Teepe, E.R.Roux, S.D.Lyman, K.Shortman, and H.J.McKenna. 1996. Dramatic increase in the numbers of functionally mature dendritic cells in Flt3 ligand-treated mice: multiple dendritic cell subpopulations identified. J. Exp. Med 184:1953-1962.

McKenna,H.J., K.L.Stocking, R.E.Miller, K.Brasel, S.T.De, E.Maraskovsky, C.R.Maliszewski, D.H.Lynch, J.Smith, B.Pulendran, E.R.Roux, M.Teepe, S.D.Lyman, and J.J.Peschon. 2000. Mice lacking flt3 ligand have deficient hematopoiesis affecting hematopoietic progenitor cells, dendritic cells, and natural killer cells. Blood 95:3489-3497.

Mollah Zia U A et al. 2003. Macrophage colony-stimulating factor in cooperation with transforming growth factor-beta1 induces the differentiation of CD34+ hematopoietic progenitor cells into Langerhans cells under serum-free conditions without granulocyte-macrophage colony-stimulating factor. The Journal of Investigative Dermatology, vol. 120, No. 2, 256-265.

Naik,S.H., A.I.Proietto, N.S.Wilson, A.Dakic, P.Schnorrer, M.Fuchsberger, M.H.Lahoud, M.O'Keeffe, Q.X.Shao, W.F.Chen, J.A.Villadangos, K.Shortman, and L.Wu. 2005. Cutting edge: generation of splenic CD8+ and CD8-dendritic cell equivalents in Fms-like tyrosine kinase 3 ligand bone marrow cultures. J. Immunol. 174:6592-6597.

O'Keeffe,M., H.Hochrein, D.Vremec, I.Caminschi, J.L.Miller, E.M. Anders, L.Wu, M.H.Lahoud, S.Henri, B.Scott, P.Hertzog, L.Tatarczuch, and K.Shortman. 2002. Mouse plasmacytoid cells: long-lived cells, heterogeneous in surface phenotype and function, that differentiate into CD8(+) dendritic cells only after microbial stimulus. J. Exp. Med 196:1307-1319.

O'Keeffe,M., H.Hochrein, D.Vremec, J.Pooley, R.Evans, S.Woulfe, and K.Shortman. 2002. Effects of administration of progenipoietin 1, Flt-3 ligand, granulocyte colony-stimulating factor, and pegylated granulocyte-macrophage colony-stimulating factor on dendritic cell subsets in mice. Blood 99:2122-2130.

Omatsu,Y., T.Iyoda, Y.Kimura, A.Maki, M.Ishimori, N.Toyama-Sorimachi, and K.Inaba. 2005. Development of Murine Plasmacytoid Dendritic Cells Defined by Increased Expression of an Inhibitory NK Receptor, Ly49Q. J Immunol 174:6657-6662.

Pulendran,B., J.Banchereau, S.Burkeholder, E.Kraus, E.Guinet, C.Chalouni, D.Caron, C.Maliszewski, J.Davoust, J.Fay, and K.Palucka. 2000. Flt3-ligand and granulocyte colony-stimulating factor mobilize distinct human dendritic cell subsets in vivo. J. Immunol. 165:566-572.

Sallusto,F. and A.Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. J Exp. Med. 179:1109-1118.

Scheicher,C., M.Mehlig, R.Zecher, and K.Reske. 1992. Dendritic cells from mouse bone marrow: in vitro differentiation using low doses of recombinant granulocyte-macrophage colony-stimulating factor. J Immunol Methods 154:253-264.

Shortman,K. and Y.J.Liu. 2002. Mouse and human dendritic cell subtypes. Nat. Rev. Immunol. 2:151-161.

Spies,B., H.Hochrein, M.Vabulas, K.Huster, D.H.Busch, F.Schmitz, A.Heit, and H.Wagner. 2003. Vaccination with plasmid DNA activates dendritic cells via Toll-like receptor 9 (TLR9) but functions in TLR9-deficient mice. J. Immunol. 171:5908-5912.

Steinman,R.M. and K.Inaba. 1999. Myeloid dendritic cells. J Leukoc. Biol. 66:205-208.

Stoll ML, Price KD, Silvin CJ, Jiang F, Gavalchin J. 2007. Immunization with peptides derived from the idiotypic region of lupus-associated autoantibodies delays the development of lupus nephritis in the (SWRxNZB)F(1) murine model.J Autoimmun. 29(1):30-7 (Epub ahead of print Apr. 2007).

Sweet,M.J., C.C.Campbell, D.P.Sester, D.Xu, R.C.McDonald, K.J. Stacey, D.A.Hume, and F.Y.Liew. 2002. Colony-stimulating factor-1 suppresses responses to CpG DNA and expression of toll-like receptor 9 but enhances responses to lipopolysaccharide in murine macrophages. J Immunol 168:392-399.

Takashima et al., 1995. Colony-stimulating Factor-1 Secreted by Fibroblasts Promotes the Growth of Dendritic Cell Lines XS Series) Derived From Murine Epidermis. J. Immunol., 154:5128-35.

Vollstedt,S., M.O'Keeffe, B.Ryf, B.Glanzmann, H.Hochrein, and M.Suter. 2006. The long-term but not the short-term antiviral effect of IFN-alpha depends on Flt3 ligand and pDC. Eur. J. Immunol. 36:1231-1240.

Vremec,D., G.J.Lieschke, A.R.Dunn, L.Robb, D.Metcalf, and K.Shortman. 1997. The influence of granulocyte/macrophage colony-stimulating factor on dendritic cell levels in mouse lymphoid organs. Eur. J. Immunol. 27:40-44.

Zheng R, Small D. 2005. Mutant FLT3 signaling contributes to a block in myeloid differentiation. Leuk Lymphoma. 46:1679-87.

* cited by examiner

INDUCTION OF DENDRITIC CELL DEVELOPMENT WITH MACROPHAGE-COLONY STIMULATING FACTOR (M-CSF)

CROSS-REFERENCE TO RELATED APPLICATIONS

This application is the U.S. National Stage of International Application PCT/EP2008/003366, filed Apr. 25, 2008, which is a continuation-in-part of U.S. application Ser. No. 11/790,798 filed Apr. 27, 2007, and claims the benefit of EP Application 07008785.3 filed Apr. 30, 2007, all of which are incorporated herein by reference.

BACKGROUND OF THE INVENTION

This invention relates to methods of inducing dendritic cell formation and methods of using induced dendritic cells as therapeutic agents.

Dendritic cells (DCs) are important decision makers within the immune system. For example, DCs initiate adaptive immune responses such as antibody production and killer cell formation. DCs also direct the quantity and quality of immune responses, for example determining whether an allergic, inflammatory, or tolerogenic immune response is to be mounted.

Many phenotypically and functionally distinct subsets of DCs exist (1). Though they are rare in the blood and immune organs, DCs include two major subgroups of different subsets, the plasmacytoid DCs (pDCs) and the conventional DCs (cDCs) (2). The cDCs in mouse include at least 3 subsets: $CD4^-CD8^+$, $CD4^+CD8^-$ and $CD4^-CD8^-$. The $CD8^+$ cDCs express the surface marker $CD8\alpha\alpha$ and are the most important cells for cross-presentation of antigens, which allows for killer cell induction against viral infection. The CD8+ cDCs can also produce large amounts of interleukin-12, an essential cytokine for inflammatory immune responses. The CD8-cDC populations are known to produce large amounts of chemokines and to be better at MHCII presentation of antigens to T cells. pDCs are anti-viral cells, that produce large amounts of the anti-viral and immune protecting cytokines, including type I Interferons (IFN-I) in response to viral DNA or viral RNA.

Like other immune cells, DCs develop from haematopoietic stem cells and later stage precursors under the influence of growth factors and cytokines. Granulocyte-Macrophage-Colony Stimulating Factor (GM-CSF) induces haematopoietic precursor cells and monocytes to develop into DCs, called GM-DCs (3-5). GM-DCs are not the majority of steady state DC subsets in lymphoid organs, though, since mice deficient for either GM-CSF or the GM-CSF receptor do not demonstrate much impairment in DC numbers (6). However, application of stabilized GM-CSF to mice in vivo results in increased levels of $CD8^-$ cDCs, but not pDCs (10). Moreover, GM-CSF has been shown to block generation of pDCs in vitro (7).

Fms-like-Tyrosine-Kinase 3-Ligand (FL) also induces development of DCs, including both cDCs and pDCs, from bone marrow (BM) precursor cells (8,9), both in vitro and in vivo (10-13). The role of FL in development of DCs (called FL-DCs) has been definitively demonstrated by the drastically reduced number of both pDCs (9) and cDCs (14) in the lymphoid organs of mice deficient in FL (FLKO).

Ex vivo isolated or FL-generated pDCs respond to direct stimulation via the Toll like receptors (TLR) 7 and 9 and their respective ligands, RNA and DNA, by producing high levels of Interferon-alpha (IFN-α). Other cell types, including cDCs, can be induced to produce IFN-α in response to active viruses or transfected DNA or RNA. IFN-α production by cDCs, though, is mediated via TLR7 and TLR9 independent pathways, including PKR, RIG-I, MDA5 and TLR-3 and as yet unidentified cytoplasmic DNA-recognition complexes (15-17). Thus, pDCs are the only cells that employ TLR7 and 9 for the high level production of IFN-α. Furthermore, certain nucleic acid molecules, such as CpG-motif containing oligonucleotides (CpG-ODN A-type), induce extremely high levels of IFN-α solely in pDCs (18). Therefore, IFN-α production in response to A-type CpG-ODN is a functional test for the presence of pDCs in mixed cell populations (17).

From studies employing GFP encoded downstream of the receptor for Macrophage Colony Stimulating Factor (M-CSF; also called CSF-1), it is clear that during differentiation of pDCs and cDC subsets the M-CSF receptor is transcribed (26). In addition, there is a report that mice deficient in M-CSF (op/op mice) have reduced numbers of DC subsets (26). Furthermore, DCs and macrophages may develop from a common progenitor cell (41). Other reports show that some DCs, though not pDCs, develop under the influence of a combination of growth factors, including M-CSF (42, 51-54). Nevertheless, while GM-CSF and FL have been shown to induce development of DCs, M-CSF has always been considered to induce development of monocytes and differentiation of macrophages, not DCs (34).

The effect of M-CSF as a therapeutic treatment has previously been investigated, though in limited situations, such as in the treatment of invasive fungal infections (39). It is not known if the patients treated with M-CSF displayed any changes in their DCs.

An increase in the number of DCs could be therapeutic in certain situations. For instance, more DCs would be helpful in fighting infections in neonatal individuals. Similarly, individuals who suffer from HIV infection, certain cancers, allergies, who have received transplants or who are immunocompromised due to radio- or chemotherapy or from taking certain drugs may have reduced numbers of DCs. In these individuals, it would be desirable to increase the numbers of DCs, including pDCs and cDCs. Thus, there is a need in the art for methods of DC induction and generation, either in vitro or in vivo.

BRIEF SUMMARY OF THE INVENTION

The invention provides Fms-like-Tyrosine-Kinase 3-Ligand-(FL)- and/or Granulocyte-Macrophage-Colony Stimulating Factor-(GM-CSF)-independent induction of DCs from precursor hematopoietic cells by M-CSF. Thus, the induction of DCs is independent of growth factors already known to induce DCs. In particular, the induction of pDCs is independent of FL, whereas the induction of cDCs is independent of GM-CSF. DCs induced by the methods of the invention are able to regulate immune responses, for example, by producing anti-viral cytokines, such as IFN-I.

The invention is based on the unexpected observation that M-CSF induces BM cultures to produce IFN-α in response to CpG. In fact, these M-CSF-induced BM cells are by phenotype and function similar to pDCs and cDCs and are called pDC and cDC.

The receptors for FL and M-CSF, Flt3 and c-fms respectively, are Group III receptor tyrosine kinases and share structural identity. Induction of DC differentiation by M-CSF, though, does not involve cross-reaction with the FL receptor, as demonstrated by experiments in which either the FL receptor or the M-CSF receptor were inhibited. Furthermore, both pDC and cDC populations developed in M-CSF BM cultures from FL knockout mice (FLKO), ruling out that M-CSF induction of these cells requires an indirect contribution of endogenous FL. Finally, when either wild type or FLKO mice were treated with M-CSF, pDCs and cDCs developed in vivo.

These results indicate that M-CSF can induce the development of pDCs and cDCs. It is possible that in natural, in vivo settings both FL and M-CSF work together to induce and regulate normal DC homeostasis. This is because infections that enhance DCs and immune conditions that result in increases or decreases in DC levels are often associated with increased levels of circulating FL and some of these same conditions have also been reported to enhance circulating M-CSF levels. For example, Langerhans cell histiocytosis demonstrates increased FL and M-CSF in the serum of patients (28), viral infections shown to increase circulating FL also increase M-CSF (29-32), the serum of Systemic Lupus Erythematosus (SLE) patients has increased FL (33), and animal models of SLE demonstrate elevated M-CSF levels (34). However, as shown here, M-CSF can clearly act independently of FL to induce DC development. It is possible that conditions exist where M-CSF is induced but not FL, or vice versa. Thus, under some conditions DC may be induced that are derived from M-CSF or FL, without the influence of the other growth factor.

The methods of the invention allow for increased levels of pDCs and cDCs after being applied to individuals in vivo. These cells can be used to defend against infections, and mount or direct immune responses. In addition, the invention provides for therapeutic and prophylactic treatments against proliferative disorders including cancers that do not involve csf-1 mutations, for example, but not limited to, Acute Myelogenous Leukemia (AML) of the type still responsive to M-CSF treatment and including those patients that are receiving therapy for overactive Flt3. The invention also encompasses M-CSF for use as a medicament. Furthermore, the invention also extends to therapeutic and prophylactic treatment against autoimmune diseases, such as SLE. Additionally, the invention is directed to M-CSF for the treatment of proliferative diseases such as cancer and autoimmune diseases such as SLE.

In an embodiment of the invention, DCs can be produced in vitro by culturing hematopoietic precursor cells in the presence of M-CSF without the presence of a further growth factor known to induce DC generation. The production of DCs are, for example, performed without co-administration of FL and/or GM-CSF.

In particular, according to the present invention a method of FL-independent pDC generation by administering M-CSF to cultured precursor cells is provided. According to this embodiment, growth factors other than FL may be present or administered with M-CSF to the precursor cell. According to the present invention, also a method of cDC generation by administering M-CSF to cultured hematopoietic precursor cells is provided, without co-administration of a further growth factor known so far to be involved in cDC generation as, for example, GM-CSF.

The hematopoietic precursor cells that can be induced are, but are not limited to, hematopoietic stem cells and progenitor cells as, for example, Common Lymphoid Progenitor (CLP). According to a preferred embodiment the precusor cell is a bone marrow cell.

In a further embodiment of the invention, DCs induced by M-CSF in vitro can be used to produce cytokines. These cytokines produced include, but are not limited to IFN-I (such as IFN-α and IFN-β), IL-1, IL-6, IL-8, IL-10, IL-12, IL-15, IL-16, IL-18, IL-23, IL-27, IL-28, IL-29, TNF-α, TNF-β and chemokines. In a preferred embodiment, the cytokine produced is interferon-α (IFN-α) The cytokines can be produced either in vitro or in vivo after the M-CSF induced DCs are introduced into an animal. In vivo, the induced DCs stimulate either innate immune responses or adaptive immune responses.

In yet other embodiments of the invention, DCs induced by M-CSF in vitro can be exposed to antigens to stimulate specific immune responses.

In further embodiments of the invention, the DCs generated by M-CSF can be used to stimulate immune responses in other immune cells.

The invention includes a method of increasing dendritic cells (DCs) in vitro, comprising culturing hematopoietic precursor cells; quantitating the number of DCs or eliminating any DCs within the bone marrow; administering Macrophage-Colony Stimulating Factor (M-CSF); quantitating the number of dendritic cells present after administration of M-CSF; wherein the number of DCs after M-CSF administration is increased over the number of DCs before administration of M-CSF. In embodiments of the invention, the precursor cells are bone marrow cells. In other embodiments of the invention, the DCs are plasmacytoid dendritic cells (pDCs) and the number of pDCs is quantitated by measuring the level of at least one cell surface marker, including but not limited to, CD11c, CD45R, CD45RA, PDCA-1, CCR9, Ly49Q, Ly6C, Siglec-H, HLA-DR, CD4, CD123, BDCA-2, BDCA-4. In other embodiments of the invention, DCs are conventional dendritic cells (cDCs), which are quantitated by measuring the level of at least one cell surface marker, including but not limited to CD11c, CD11b, CD4, CD8, Sirp-alpha, DEC-205, MHCII, 33D1, HLA-DR, BDCA-1, BDCA-3, and CLEC9A. In other embodiments of the invention, M-CSF is administered in a poxvirus vector, in particular in a vaccinia virus vector, including but not limited to an MVA vector. In other embodiments of the invention, M-CSF is administered in another viral vector. In yet other embodiments of the invention, the method of increasing DCs further comprises stimulating the DCs by exposing them to a stimulatory agent, wherein the stimulatory agent includes, but is not limited to, a TLR-agonist, virus, bacteria, fungi, plant, or parts thereof, or cytokines including but not limited to IFN-I, IL-10, IL-12, IL-6, and TNF-α. Embodiments of the invention also include a step of reintroducing the harvested dendritic cells into the animal. In yet other embodiments of the invention, the DCs can be pDCs or cDCs or both.

Another embodiment of the invention is a method of increasing dendritic cells in an animal, comprising co-administering M-CSF with an antigen to the animal; wherein the co-administration results in an increase in the number of DCs in the animal. The invention encompasses DCs that are pDCs or cDCs. Further embodiments of the invention include antigens that are derived from tumors, viruses, bacteria, fungi, parasites, prions, plants, molluscs, arthropods, or vertebrate toxins. In other embodiments of the invention the animal is a mouse or a human. In other embodiments of the invention, M-CSF is administered in a poxvirus vector, including, but not limited to an MVA vector. In other embodiments of the invention, M-CSF is administered in another viral vector. In yet another embodiments of the invention, M-CSF is administered in a plasmid or via RNA.

Yet another embodiment of the invention is a method of producing dendritic cells, comprising culturing hematopoietic precursor cells; administering M-CSF to the cultured cells; generating dendritic cells; and harvesting the dendritic cells. The DCs can be pDCs or cDCs. In embodiments of the invention, the method can further comprise exposing the dendritic cells to an antigen. The invention encompasses antigens including, but not limited to antigens that are derived from tumors, viruses, bacteria, fungi, parasites, prions, plants, molluscs, arthropods, or vertebrate toxins. Embodiments of the invention also include removing the precursor cells from an animal and reintroducing the harvested dendritic cells into the animal. The invention also includes embodiments in which the M-CSF is administered to the cultured cells as a polypeptide or as a nucleic acid that is expressed in the cultured cells wherein the nucleic acid is DNA or RNA. The invention also includes methods wherein the M-CSF is administered to the cultured cells in a poxvirus vector, in particular in a vaccinia virus vector, including, but not limited to, a Modified Vaccinia virus Ankara (MVA) viral vector.

A further embodiment of the invention includes a method of inducing an immune response to one or more antigens in an animal, comprising removing hematopoietic precursor cells from an animal; culturing the precursor cells; administering M-CSF to the cultured cells; generating dendritic cells; exposing the dendritic cells to antigens; harvesting the primeti dendritic cells; and reintroducing the primed dendritic cells into the animal. In the invention, the antigens are derived from tumors, viruses, bacteria, fungi, parasites, prions, plants, molluscs, arthropods, or vertebrates, including toxins. Embodiments of the invention also include administering the antigen to the animal. In yet other embodiments of the invention the animal is a human patient suffering from a proliferative disorder and/or an autoimmune disease. In particular, the patient is suffering from Systemic Lupus Erythematosus (SLE) and the antigens include peptides based on the anti-idiotypic or complementarity determing regions (CDR) of SLE-associated autoantibodies (45, 46).

Embodiments of the invention also include an animal that is a human patient suffering from Acute Myeloid Leukemia (AML) or acute lymphoblastic leukemia (ALL) undergoing chemotherapy to inhibit Flt3 or c-kit and the antigen could include novel peptides derived from the patients mutated or duplicated Flt3 or c-kit that are not present in the normal form of these receptors (47).

Another embodiment of the invention is a method of producing interferon-α (IFN-α), comprising culturing hematopoietic precursor cells; administering M-CSF to the cultured cells; and collecting the IFN-α.

Yet another embodiment of the invention is a method of treating a patient suffering from a proliferative disorder and/or an autoimmune disease, comprising administering M-CSF to the patient, and increasing the number of DCs in the patient.

A further embodiment of the invention is a method of treating a patient suffering from AML, ALL and/or SLE, comprising administering M-CSF to said patient and increasing the number of DCs in the patient.

The invention also encompasses M-CSF and its use as a medicament. Specifically, the invention is directed to M-CSF for the treatment of proliferative diseases such as cancer or leukemia, in particular AML and/or ALL, and/or for the treatment of autoimmune diseases such as SLE.

Yet another embodiment of the invention is a method of stimulating an immune response, comprising culturing a hematopoietic precursor cell; administering M-CSF to the cultured cell; generating a DC; and exposing the DC to an immune cell, wherein the immune cell is stimulated to produce an immune response. The DCs can be pDCs or cDCs. The DCs are preferably generated as described herein above, i.e., the DCs should be generated without co-administration of a further growth factor known so far to induce DC generation as, for example, FL and/or GM-CSF. In a further embodiment, pDCs are generated FL-independent, but may be generated by co-administering other growth factor, whereas cDCs may be generated without addition of other growth factors known to be involved in their generation as, for example, GM-CSF. The immune cells can be T-cells (including, but not limited to regulatory T-cells, suppressor T-cells, or Killer T-cells), T-helper cells (including, but not limited to, a Th1, Th2, or Th17 cell), B-cells, Natural Killer Cells, or macrophages. Stimulation of an immune response can be achieved in vitro or in vivo. Furthermore, the immune response can be an anti-allergic immune response, an antiseptic immune response, an anti-graft immune response, an anti-tumor immune response, an anti-autoimmune response, a tolerogenic immune response, an anti-pathogen immune response, or a regulatory immune response.

Another embodiment of the invention relates to a dendritic cell generated from a hematopoietic precursor cell by M-CSF stimulation of said precursor cell. The dendritic cell can be a plasmacytoid dendritic cell, pDC, or a conventional dendritic cell, cDC. The dendritic cell generation preferably occurs without a further growth factor known to induce DCs as, for example, FL and/or GM-CSF.

A further embodiment of the invention relates to a recombinant poxvirus comprising a nucleic acid sequence coding for M-CSF. Specifically, said nucleic acid sequence is included in the viral genome of said poxvirus. Preferably, coding sequences of growth factors known to be involved in DC generation, in particular the coding sequences of FL and/or GM-CSF, are absent in the recombinant poxvirus. The poxvirus includes but is not limited to Vaccinia virus, in particular Modified Vaccinia Virus Ankara (MVA).

In a preferred embodiment, said MVA is characterized by having at least one of the following properties:

(i) capability of reproductive replication in vitro in chicken embryo fibroblasts (CEF) but no capability of reproductive replication in the human keratinocyte cell line (HaCaT), the human embryo kidney cell line (293), the human bone osteosarcoma cell line (143B), and the human cervix adenocarcinoma cell line (HeLa), (ii) failure to replicate in a mouse model that is incapable of producing mature B and T cells and as such is severely immune compromised and highly susceptible to a replicating virus, and (iii) induction of at least the same level of specific immune response in vaccinia virus prime/vaccinia virus boost regimes when compared to DNA-prime/vaccinia virus boost regimes.

According to further embodiments of the invention, the MVA is characterized by having at least two or all three of the advantageous properties.

In a particularly preferred embodiment, the MVA is an MVA Vaccinia virus as deposited at the European Collection of Cell Cultures (ECACC) Salisbury (UK) under number V00083008 and derivatives thereof. The virus as deposited is hereinafter also referred to as MVA-BN.

The recombinant poxvirus as outlined above may also further comprise a heterologous nucleic acid sequence selected from a sequence coding for at least one antigen and/or antigenic epitope.

The present invention also relates to pharmaceutical compositions or vaccines comprising such a recombinant poxvirus and, optionally, a pharmaceutically acceptable carrier, diluent and/or additive.

In a further embodiment, the invention relates to the recombinant poxvirus comprising a nucleic acid sequence coding for M-CSF, preferably the recombinant as described above, for use as a medicament or as a vaccine. Furthermore, the invention also encompasses a recombinant poxvirus comprising a nucleic acid sequence coding for M-CSF as outlined herein for the treatment of proliferative diseases and/or autoimmune diseases. Proliferative diseases have already been specified hereinabove and include, but are not limited to cancer and leukemias. In a preferred embodiment, said type of leukemia is AML. Autoimmune diseases have also been specified in the present application and include, but are not limited to, SLE.

In another embodiment, the present invention relates to the use of the recombinant poxvirus and/or the pharmaceutical composition for the generation of dendritic cells (DCs) from hematopoietic precursor cells.

A further embodiment of the invention is a kit for inducing an immune response to an antigen in an animal, said kit comprising, preferably in a first vial, M-CSF, preferably in the manner as described above, i.e., without a growth factor known to induce DC generation, as FL and/or GM-CSF, and/or comprising a recombinant poxvirus including a nucleic acid sequence encoding M-CSF, preferably the recombinant as described above, and an antigen, preferably contained in a second vial. In a preferred embodiment of said kit, the recombinant poxvirus is administered to an animal for generating and/or increasing dendritic cells (DCs) and said antigen is subsequently administered to said animal after DCs have been generated and/or induced.

BRIEF DESCRIPTION OF THE DRAWINGS

FIG. 7 depicts surface phenotype of M-CSF-derived cDCs (M-cDCs) Stained cells from day 6 M-CSF cultures (filled histograms), FL cultures (grey open histograms) or freshly isolated spleen DCs (black histograms) were gated on cDCs by selecting for the expression of CD11c and lack of CD45RA or CD45R amongst the PI negative cells. The expression of a range of surface markers on the cDC surface is shown. The light grey histograms represent the background staining of the M-cDCs within each stain. All M-cDCs also lacked expression of CD3, CD19, CD49b and NK1.1. The surface phenotypes shown are from one experiment representative of two to five experiments for M-cDC, two to three experiments for FL-cDCs and two experiments for spleen cDCs.

DETAILED DESCRIPTION OF THE PREFERRED EMBODIMENTS

Figure 3:
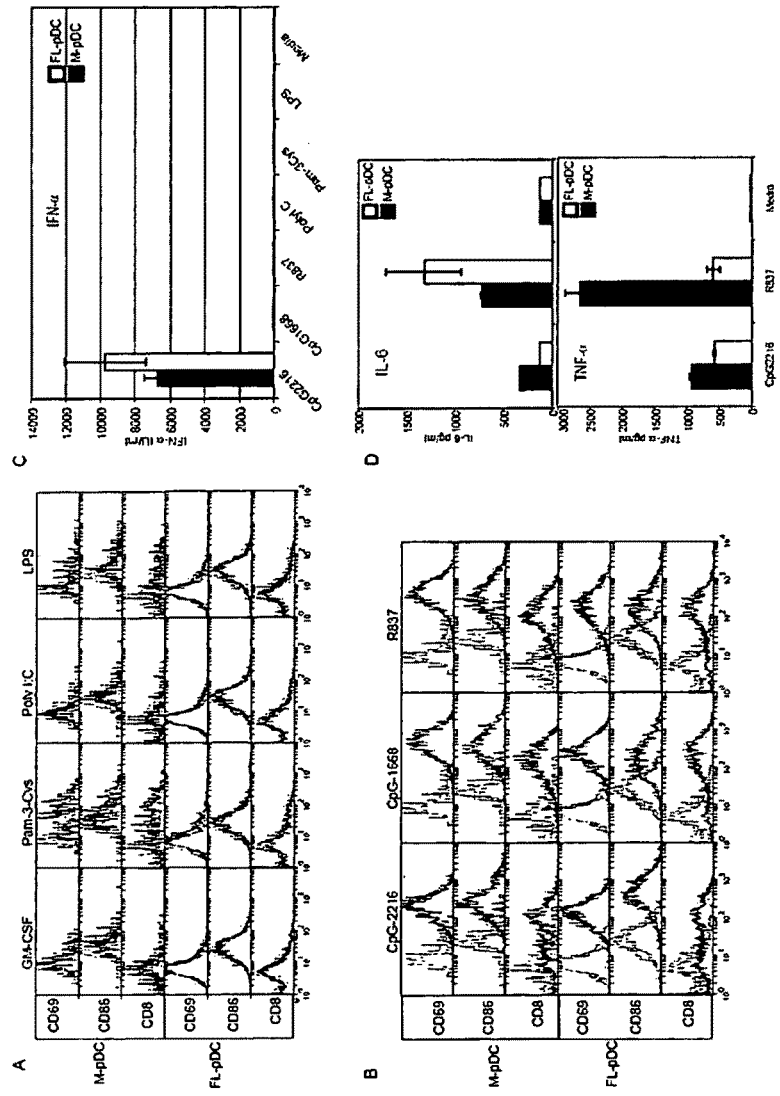
FIG. 3. M-pDC are activated and produce IFN-α in response to TLR9 stimulation and other cytokines in response to TLR7 stimulation. Highly purified, sorted M-pDC or FL-pDC were incubated for 18 hrs with the TLR ligands shown. The surface phenotype of the pDC were analysed (A & B), grey histograms indicate surface expression levels of cells cultured in media only and black histograms the expression levels of cells cultured in the stimuli indicated. Supernatants were assayed by ELISA for the presence of IFN-α (C) or by Cytometric Bead Assay (CBA) for the production of IL-6 and TNF-α (D). No IFN-γ, IL-10, IL-12p70 or MCP-1 was detected by CBA in the M-pDC supernatants. The data shown are from one experiment representative of 3 experiments (A&B), 5 experiments (C) and 3 experiments (D). Error bars represent the range of duplicate samples.
Figure 4:
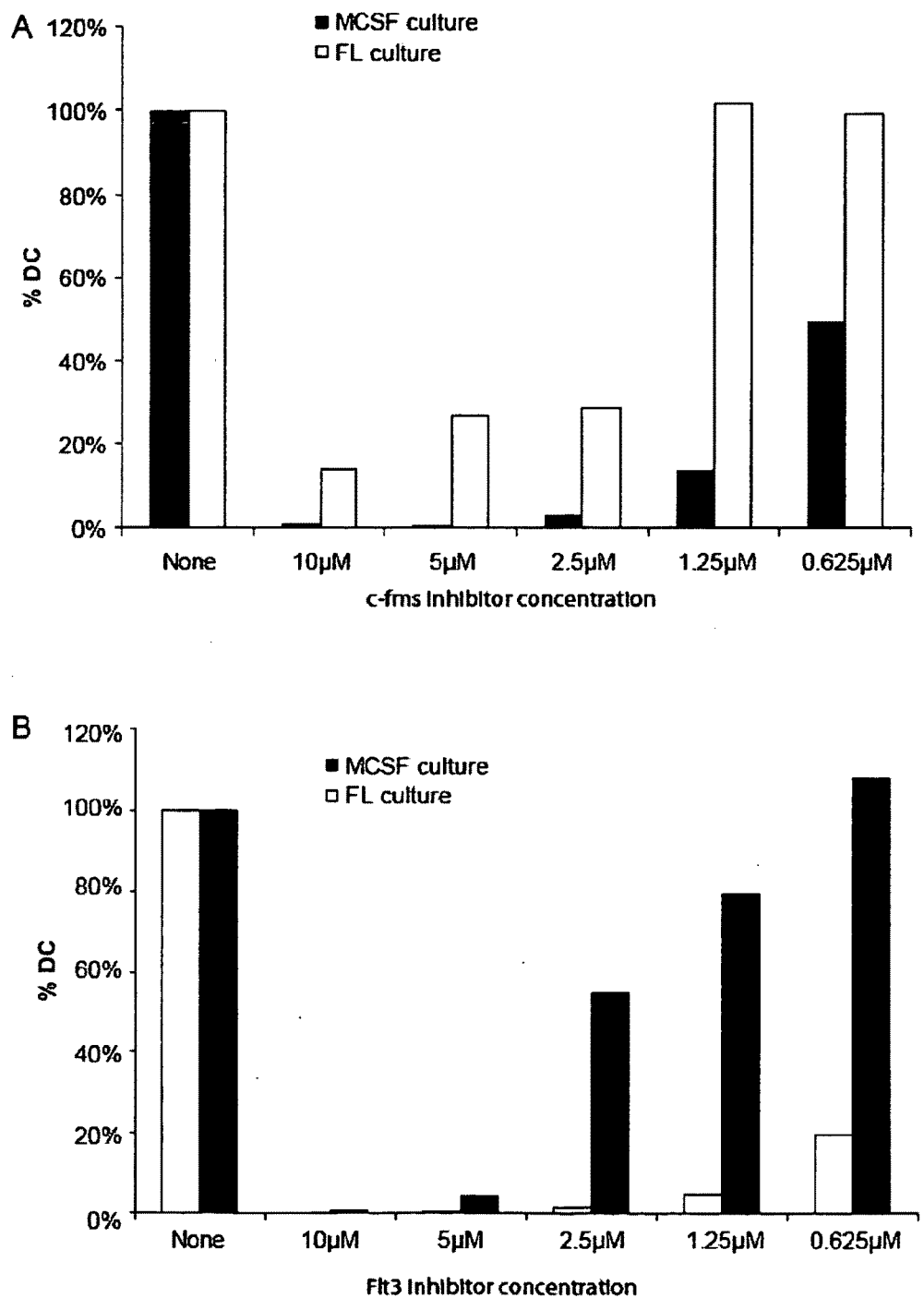
FIG. 4 and FIG. 8. The generation of M-DC is inhibited by a c-FMS inhibitor. Replicate M-CSF and FL cultures were conducted in parallel in the presence or absence of a range of A: cFMS Receptor Tyrosine Kinase Inhibitor or B: Flt3 Inhibitor concentrations. At the end of the culture period all cells were counted. The number of cells harvested from cultures without inhibitor was set at 100%. Cells from cultures containing inhibitor were expressed as a percentage of cells obtained in the absence of inhibitor. The data shown in each panel are from one experiment each, representative of 2 experiments carried out for each of the inhibitors.
Figure 5:
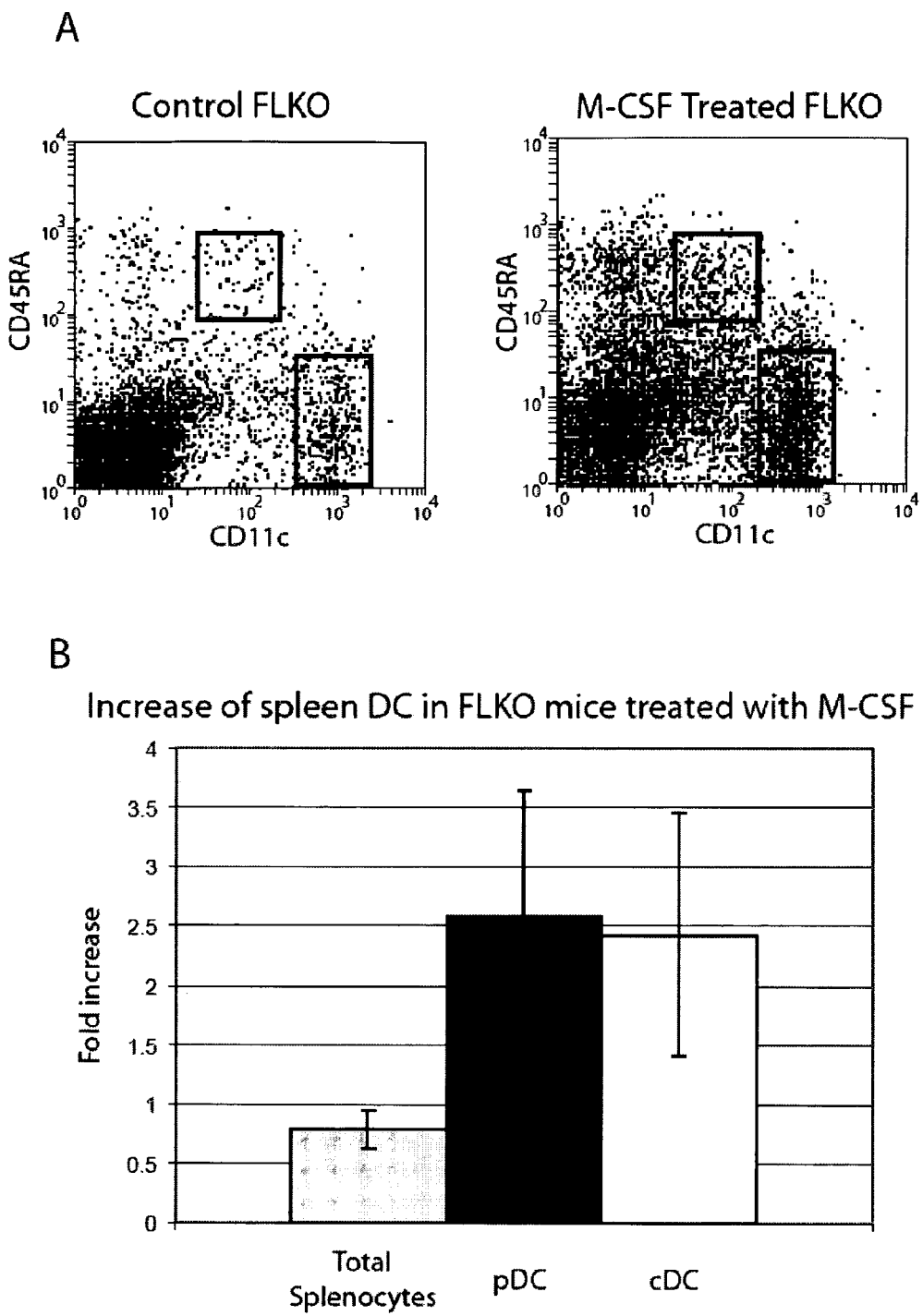
FIG. 5. M-CSF treatment increases DC numbers in vivo. FLKO mice were treated for 5 consecutive days ip with 10 μg/day M-CSF in 0.01% BSA in PBS or with vehicle alone (control). DC were purified from FLKO spleens and stained with CD11c and CD45RA and shown gated in A. Total splenocytes and pDC and cDC populations were enumerated and are shown as a fold increase compared to vehicle treated mice (B). Data are pooled from 3 individual mice within 2 separate experiments compared to control mice analysed the same day.
Figure 6:
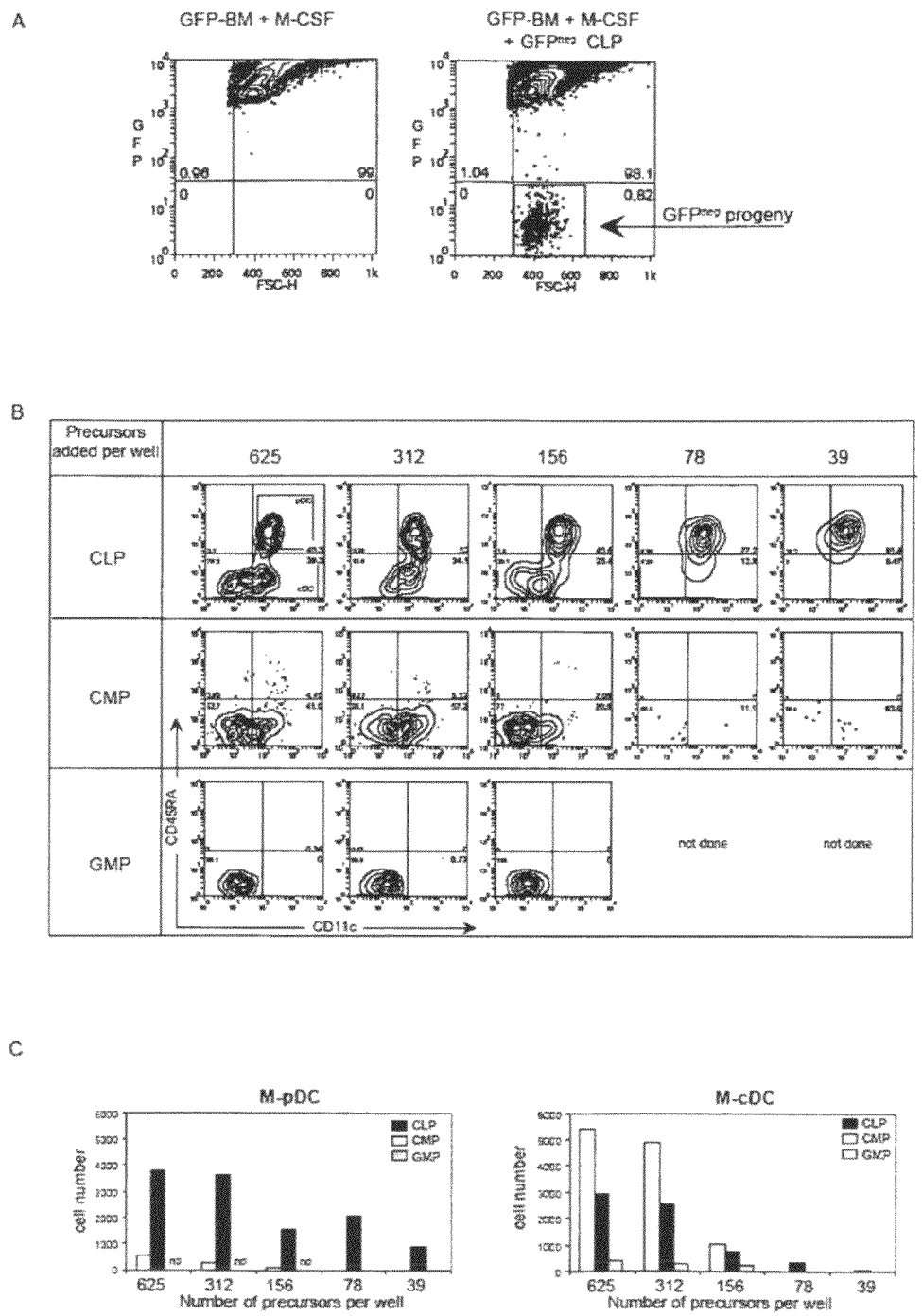
FIG. 6. CLP are major producers of M-pDC and CMP produce mainly M-cDC. Within control M-CSF cultures containing only UBC-GFP BM cells, all cells expressed high levels of GFP and fluoresced strongly in the FITC (GFP) channel (A, left panel). The progeny of C57BL/6 progenitors spiked into UBC-GFP BM cultures were gated as FITC/GFP$^{neg}$ cells (A, right panel). Serial dilutions of CLP, CMP or GMP (625 to 39 cell equivalents are shown) were added to $1.0 \times 10^6$ UBC-GFP BM cells in 1 ml and M-CSF cultures were carried out for 6 days. GFP$^{neg}$PI$^{neg}$ cells were gated and stained with CD45RA and CD11c. The resulting M-DC plots are shown in B and the gates used to determine M-pDC and M-cDC are shown in the top left contour. The absolute number of M-pDC and M-cDC obtained in the cultures of B are shown in C. Data shown are from one experiment. Similar results were obtained in a second experiment.
Figure 7:
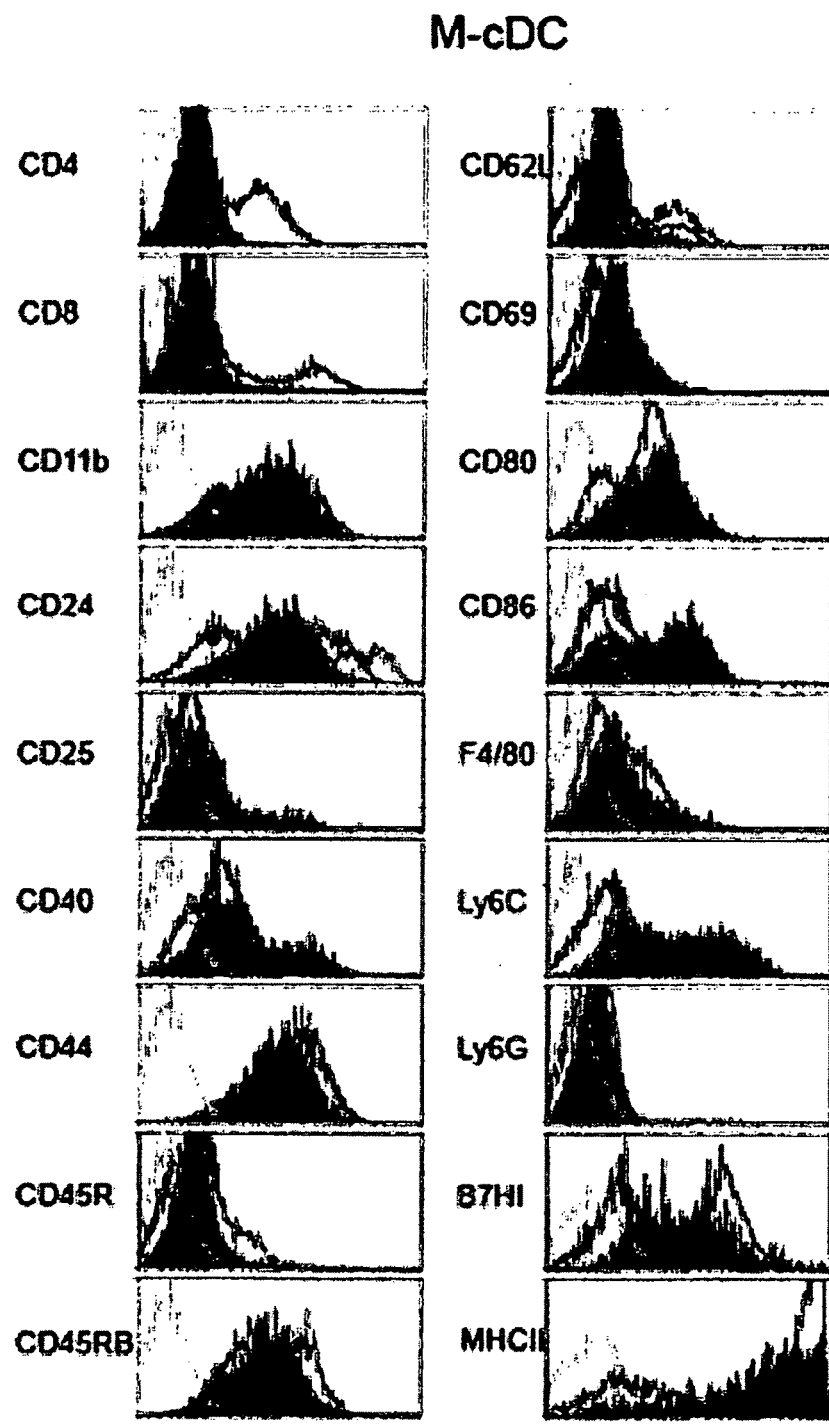
FIG. 7. Surface phenotype of M-cDC compared to FL-derived cDCs (FL-cDCs) and ex-vivo isolated spleen cDCs.

The invention is supported by experimental results showing that M-CSF induces IFN-α production (FIG. 1) and the development of pDCs and cDCs from hematopoietic precursor cells in vitro (FIG. 2), in the absence of FL. These M-CSF induced pDCs and cDCs are phenotypically identical to pDCs and cDCs induced by FL or those that develop in vivo, (FIGS. 3 and 5) and produce antiviral cytokines, such as IFN-I (FIG. 4). Furthermore, inhibition of the M-CSF receptor demonstrates that M-CSF inducing activity occurs through its own receptor and not as a cross-reaction with the FL receptor, flt3 (FIG. 6). Finally, M-CSF has been shown to induce pDCs and cDCs in vivo, in an FL-independent pathway (FIG. 7).

In describing the embodiments of the invention the term "induction" refers to the introduction of a signal that results in a change in the morphology and or physiology of a cell. The term "development" refers to the alteration of cell morphology and physiology along a genetically determined pathway. The term "differentiation" refers to the development of a cell from a precursor cell to a more specialized cell type. The term "cell surface marker" refers to a protein or other molecule on the surface of a cell that is specific for that cell, either from any other cell or from other cells in the developmental pathway of the cell. The term "precursor cell" refers to a less differentiated cell that has the ability to develop into a more differentiated cell after induction by some signal. The term "hematopoietic precursor cell" refers generally to precursor cells suitable for DC generation and does, thus, encompass, for example, hematopoietic stem cells, but also progenitor cells as, for example, Common Lymphoid Progenitor (CLP). Hematopoietic precursor cells include, but are not limited to, bone marrow cells.

In an embodiment of the invention, DCs are produced in vitro. Hematopoietic precursor cells can be cultured and DCs harvested by techniques known to those of skill in the art, as exemplified, but not limited to, the procedures described in Example 1 below. The number of DCs can be quantitated directly. For example, the number of DCs can be quantitated by measuring DC cell surface antigens, for example, Ly49Q, CD4, MHCII, B7H1, CD81, CD62L, and CD11 b, CD45RA, and F4/80, by techniques known to those of skill in the art. These techniques include, but are not limited to, surface staining and fluorescence activated cell sorting (FACS), for example by the methods described in Example 1 below. The number of DCs can also be quantitated indirectly. For example, the number of DCs can be quantitated by measuring DC-specific increases in cytokine production. Quantitation of cytokine production, IFN-I, IFN-α, IL-12 p70, IL-6, TNF-α, MCP-1 and IFN-γ, can be achieved with techniques known to those of skill in the art. These techniques include, but are not limited to, ELISA, as described in Example 1, below. Fold increases in cytokine production can include, but are not limited to, greater than or equal to 1.2 fold, greater than or equal to 1.5 fold, greater than or equal to 2 fold, greater than or equal to 3 fold, greater than or equal to 4 fold, greater than or equal to 5 fold, or greater than or equal to 10 fold.

In embodiments of the invention M-CSF and/or antigen can be administered to cultured cells as a protein. M-CSF protein can be produced by methods known to those of skill in the art, including, but not limited to, in vitro, prokaryotic, and eukaryotic expression systems.

In embodiments of the invention, M-CSF can be administered in vitro to cultured cells at levels including, but not limited to, 1-100 ng/ml, 1-75 ng/ml, 1-50 ng/ml, 1-25 ng/ml, 1-10 ng/ml, 10-100 ng/ml, 10-75 ng/ml, 25-100 ng/ml, 50-100 ng/ml, 75-100 ng/ml, 25-75 ng/ml, or 50-75, ng/ml, preferably at 10-50 ng/ml, and most preferably at 20 ng/ml.

M-CSF and/or antigen can also be administered to cultured cells by introduction of a DNA or RNA that encodes M-CSF and directs its expression within the cultured cell. Techniques for this method of administration include, but are not limited to, techniques for transfection, lipofection, electroporation, and transduction. M-CSF can also be administered to a cell by infection with a virus that carries the genetic information to produce M-CSF. Non-limiting examples of such a virus are DISC-Herpes virus and poxviruses, including, but not limited to Modified Vaccinia virus Ankara (MVA).

As described in WO publication 02/42480, which is specifically incorporated by reference herein, novel MVA strains with enhanced safety have been developed. These strains are characterized by having at least one of the following advantageous properties:

(i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa;

(ii) failure to replicate in a mouse model that is incapable of producing mature B and T cells and as such is severely immune compromised and highly susceptible to a replicating virus; and (iii) induction of at least the same level of specific immune response in vaccinia virus prime/vaccinia virus boost regimes when compared to DNA-prime/vaccinia virus boost regimes.

One of the developed strains has been deposited at the European Collection of Animal Cell Cultures (ECACC) with the deposit number V00083008. This strain is referred to as "MVA-BN" throughout the specification of WO 02/42480.

The term "not capable of reproductive replication" means that the virus shows an amplification ratio of less than 1 in human cell lines, such as the cell lines 293 (ECACC No. 85120602), 143B (ECACC No. 91112502), HeLa (ATCC No. CCL-2) and HaCat (Boukamp et al., *J. Cell Biol.* 106(3): 761-71 (1988)), under the conditions as outlined in Example 1 of WO 02/42480 for some specific MVA strains.

According to WO 02/42480, "failure to replicate in vivo" refers to viruses that do not replicate in humans and in the mice model as described in the WO 02/42480 publication.

Those of skill in the art are knowledgeable of these methods of administration. Administration of the M-CSF or antigen to the DC "exposes" the DC to the M-CSF or antigen.

In other embodiments of the invention, antigens can be co-administered to the DCs with M-CSF. These antigens include, but are not limited to, antigens present on viruses (in non-limiting example, influenza, HIV, CMV, EBV, human papilloma virus, adenovirus, HBV, HCV and vaccinia), bacteria, fungi, parasites, prions, and tumor cells (tumor antigens), as well as toxin antigens from viruses, bacteria, fungi, parasites, molluscs, arthropods, and vertebrates. In embodiments of the invention antigens can also include peptides from autoantibodies which can be antigens for the treatment of SLE, and peptides corresponding to the mutant forms of Flt3 or c-kit which can be antigens for the treatment of AML.

The term "co-administration" refers to the administration of more than one substance to an animal or to cultured cells. Co-administration can occur simultaneously or in series, with one substance administered before the other. When administered in series, the second substance can be, but is not limited to, within 1 minute, 2, minutes, 5 minutes, 10 minutes, 30 minutes, 1 hour, 2 hours, 8 hours, 12 hours, 24 hours, 2 days, 3 days, 7 days, 14 days, or 1 month. In embodiments of the invention, DCs generated by administration of M-CSF are also "exposed" to antigen by the co-administration of the antigen.

The term "tumor antigen" refers to an antigen associated with certain tumoral diseases. Tumor antigens are most often antigens encoded by the genome of the host that develops the tumor. Thus, in a strict sense tumor antigens are not foreign antigens. However, tumor antigens are found in significant amounts in tumors; whereas, the amount of tumor antigens in normal tissues is significantly lower, and most often no tumor antigens are found at all in normal tissue. Examples of tumor antigens include gp75 antigen for melanoma papilloma virus proteins for cervical cancer, and tumor specific idiotypic proteins for B cell lymphomas.

In further embodiments of the invention, M-CSF generated DCs are used to stimulate immune responses in other immune cells in vivo or in vitro. These immune cells include, but are not limited to, T-cells (including, but not limited to, regulatory or suppressor T-cells, Killer T-cells (CTLs), and T-Helper cells (including, but not limited to Th1, Th2, and Th17), B cells, Natural Killer cells (NK cells), and macrophages. The stimulated cells can be introduced into an animal in vivo to mount an immune response. Such immune responses include, but are not limited to, anti-allergic responses, anti-septic responses, anti-graft rejection responses, anti-tumor responses, anti-autoimmune disease responses, tolerogenic immune responses, anti-pathogenic immune responses, and regulatory immune responses.

M-CSF generated DCs can also be exposed to stimulatory agents, wherein "stimulatory agents" are proteins and other molecules that induce a specific response from DCs. Stimulatory agents of the invention include, but are not limited to, TLR-agonists, viruses, bacteria, fungi, plants, parasites or parts thereof, or cytokines including but not limited to IFN-I, IL-6, IL-10, IL-12 and TNF-α.

In other embodiments of the invention M-CSF is administered to an animal. The term "animal" includes, but is not limited to vertebrates, most preferably mammals, including, but not limited to humans, horses, cows, pigs, sheep, goats, llamas, cats, dogs, mice, and rats.

In other embodiments of the invention, antigens can be co-administered with M-CSF. These antigens include, but are not limited to, antigens present on viruses (in non-limiting example, influenza, HIV, CMV, EBV, human papilloma virus, adenovirus, HBV, HCV and vaccinia), bacteria, fungi, parasites, prions, and tumor cells (tumor antigens), as well as toxin antigens from viruses, bacteria, fungi, parasites, mollosucs, arthropods, and vertebrates. In embodiments of the invention antigens can also include peptides from autoantibodies which can be antigens for the treatment of SLE, and peptides corresponding to the mutant forms of Flt3 or c-kit, which can be antigens for the treatment of AML.

M-CSF and/or antigen can be administered to an animal as a protein, DNA, RNA, or virus. Administration of a protein to an animal can be achieved by, but is not limited to, oral, transdermal, transmucosal administration, or by injection (parenteral). The dose administered can vary depending on which type of administration is used. Pharmaceutically acceptable formulations of M-CSF and antigen are known in the art. Carriers or excipients can be used to produce pharmaceutical compositions. Examples of carriers include, but are not limited to, calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include, but are not limited to sterile solutions of water for injection (WFI), saline solution, and dextrose. M-CSF can be administered by different routes, including but not limited to, intravenous, intraperitoneal, subcutaneous, intramuscular, oral, transmucosal, rectal, or transdermal.

In vivo, M-CSF and/or antigen is administered to an animal at levels of 0.01 µg-100 mg/day, 0.1 µg-100 mg/day, 1 µg-100 mg/day, 10 µg-100 mg/day, 100 µg-100 mg/day, 1 mg-100 mg/day, 10 mg-100 mg/day, 50-100 mg/day, 0.01 µg-10 mg/day, 0.1 µg-10 mg/day, 1 µg-10 mg/day, 10 µg-10 mg/day, 100 µg-10 mg/day, 1-10 mg/day, 10-50 mg/day, 0.01 µg-1 mg/day, 0.1 µg-1 mg/day, 1 µg-1 mg/day, 10 µg-1 mg/day, 100 µg-1 mg/day, 1-10 mg/day, or 1-50 mg/day. Levels of 1-20 µg/day are preferable and 10 µg/day most preferable for administration to rodents. Levels of 1-50 mg/day are preferable, and 25 mg/day most preferable, for humans. M-CSF can also be administered to animals on a per weight basis, including, but not limited to, 0.5 µg-10 g/g weight/day, 1 µg-10 g/g weight/day, 10 µg-10 g/g weight/day, 100 µg-10 g/g weight/day, 1 g-10 g/g weight/day, 0.5 µg-1 g/g weight/day, 1 µg-1 g/g weight/day, 10 µg-1 g/g weight/day, or 100 µg-1 g/g weight/day, preferably 0.5 µg/g weight/day. Other dosages are contemplated by the invention, and can be determined using assays known to the skilled artisan.

Further embodiments of the invention include administration of M-CSF to precursor cells, preferably in the manner as described herein above, wherein said precursor cells have been isolated from an animal. These cells are induced by M-CSF in vitro, exposed to antigen, and returned to the animal for a therapeutic or prophylactic effect. Techniques for such "ex vivo" therapies are known to those in the art, as described (36, 37, 44). Other techniques for ex vivo therapy are also contemplated for the invention.

To induce hematopoietic precursor cells in vitro the cells can be cultured and DCs harvested by techniques known to those of skill in the art, as exemplified, but not limited to, the procedures described in Example 1 below. In this embodiment the DCs are characterized by observing DC cell surface antigens, for example CD11c, Ly49Q, CD4, CD8, CD22, DEC-205, 33D1, PDCA-1, BDCA-1, BDCA-2, BDCA-4, CD25, CD80, CD86, CD40, CD69, Siglec-H, Ly6C, CCR9, HLA-DR, CD123, MHCII, B7H1, CD81, CD62L, CD11b, CD45R, CD45RA, and F4/80, by techniques known to those of skill in the art. These techniques include, but are not limited to, surface staining and fluorescence activated cell sorting (FACS), for example by the methods described in Example 1 below. Quantitation of cytokine production can also be used, including, but not limited to, IFN-I, IFN-α, IL-12 p70, IL-6, TNF-α, MCP-1 and IFN-γ. This is achieved with techniques known to those of skill in the art. These techniques include, but are not limited to, ELISA, as described in Example 1, below.

In embodiments of the invention involving ex vivo therapies, M-CSF and/or antigen can be administered to cultured cells as a protein in vitro. M-CSF protein can be produced by methods known to those of skill in the art, including, but not limited to, in vitro, prokaryotic, and eukaryotic expression systems.

In embodiments of the invention, M-CSF and/or antigen is administered in vitro to cultured cells at levels including, but not limited to, 1-100 ng/ml, 1-75 ng/ml, 1-50 ng/ml, 1-25 ng/ml, 1-10 ng/ml, 10-100 ng/ml, 10-75 ng/ml, 25-100 ng/ml, 50-100 ng/ml, 75-100 ng/ml, 25-75 ng/ml, or 50-75, ng/ml, preferably at 10-50 ng/ml, and most preferably at 20 ng/ml.

M-CSF and/or antigen can also be administered to cultured cells by introduction of a DNA or RNA that encodes M-CSF and directs its expression within the cultured cell. Techniques for this method of administration include, but are not limited to, techniques for transfection, lipofection, electroporation, and transduction. M-CSF and/or antigen can also be administered to a cell by infection with a virus that carries the genetic information to produce M-CSF and/or the antigen. Non-limiting examples of such viruses are DISC-Herpes virus and poxviruses, including, but not limited to, Vaccinia virus, in particular Modified Vaccinia virus Ankara (MVA). A strain of MVA, MVA-BN, is deposited at the European Collection of Animal Cell Cultures (ECACC) with the deposit number V00083008. Those of skill in the art are knowledgeable of these methods of administration.

Some autoimmune diseases, for example, but not limited to, SLE have been shown to be mediated by the Toll-like receptor 9 (TLR9) (38). TLR9 recognizes DNA and, under certain conditions, can recognize self-DNA in autoimmune disease. In these diseases, B-cells that express TLR9 will proliferate when TLR9 binds to self DNA. In addition, pDCs are also activated by the TLR9-DNA complexes and produce increased levels of IFN-I, which further aggravates the disease. FL induction of pDCs contributes to this aggravation by adding constant stimulation when it induces pDC development. An embodiment of the invention provides a better therapeutic regime, wherein M-CSF is administered to a patient suffering from an autoimmune disease, for example SLE, which acts to prime the new DCs induced by M-CSF. In contrast to treatment with FL, though, not only are DCs induced, but M-CSF also down-regulates TLR9 and its responses to self-DNA complexes (23). Thus, M-CSF-induced DCs can promote specific immune responses in the patient, including but not limited to, down modulation of exaggerated auto-immune reactions, without triggering additional TLR9 IFN-I production and B-cell stimulation.

In another embodiment of the invention, a therapeutic regime for proliferative disorders is provided. Such proliferative disorders include cancer types such as leukemias. These leukemias include, but are not limited to, AML. AML and other leukemias are mediated by activation of Flt3, the receptor for FL (39, 48-50). Thus, in this embodiment of the invention, administration of FL to a patient to induce development of DCs would aggravate the disease. In contrast, the invention provides for administration of M-CSF, along with a tumor antigen, to a patient with leukemia, including, but not limited to AML, so that DCs can be induced to provide an immune response against the tumor cells, without further stimulation of the tumor cells with FL. An inhibitor of Flt3 can also be used together with M-CSF to treat the leukemias. Inhibitors of Flt3 are known to the person skilled in the art.

Embodiments of the invention are also directed to the treatment of other proliferative disorders including, but not limited to, hematopoietic neoplastic disorders involving hyperplastic/neoplastic cells of hematopoietic origin arising from myeloid, lymphoid or erythroid lineages, or precursor cells thereof. These include, but are not limited to erythroblastic leukemia, acute promyeloid leukemia (APML), chronic myelogenous leukemia (CML), lymphoid malignancies, including, but not limited to, acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to, non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

In addition, embodiments of the invention include, but are not limited to, the treatment of malignancies of epithelial or endocrine tissues, including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include, but are not limited to, those forming from tissue of the cervix, lung, prostate, breast, head and neck, colon and ovary.

Furthermore, embodiments of the invention include a dendritic cell generated from a hematopoietic precursor cell by M-CSF stimulation of said precursor cell. The generated dendritic cell may be of the cDC- and/or the pDC-type. Stimulation of the precursor cell may occur in the presence of M-CSF and other growth factors excluding FL when generating pDCs and/or excluding GM-CSF when generating cDCs. The hematopoietic precursor cell includes, but is not limited to, bone marrow cells. Methods for generating dendritic cells by M-CSF stimulation are extensively described herein.

The invention further relates to a recombinant poxvirus comprising a nucleic acid sequence coding for M-CSF. Preferably, the coding sequence of growth factor known to induce DC generation, in particular the coding sequence of FL and/or GM-CSF, is absent in the recombinant virus.

According to the present invention the poxvirus may be any poxvirus. Thus, the poxvirus may be any virus of the subfamily of Chordopoxvirinae and Entomopoxvirinae (see Fields Virology 3rd edition, Lippincott-Raven Publishers, Philadelphia, USA, Chapter: 83, ISBN 0-7817-0253-4). Viruses from the subfamily Chordopoxvirinae are particularly preferred if the recombinant poxvirus is used to express genes in mammalian animals, including humans. Particularly preferred genera belonging to the subfamily Chordopoxvirinae are Orthopoxviruses, Parapoxviruses, Avipoxviruses, Capripoxviruses, Leporipoxviruses and Suipoxviruses. Most preferred are Orthopoxviruses and Avipoxviruses. Examples for avipoxviruses are canarypoxviruses and fowlpoxviruses. An example for an Orthopoxvirus is vaccinia virus. The vaccinia virus strain that may be used according to the present invention may be any vaccinia virus strain, such as strains Copenhagen, Wyeth, Western Reserve, Elstree, NYCBH and so on. Particularly preferred is Modified Vaccinia Ankara (MVA).

MVA has been generated by 516 serial passages on chicken embryo fibroblasts of the Ankara strain of vaccinia virus (CVA) (for review see Mayr, A., et al. Infection 3, 6-14 [1975]). As a consequence of these long-term passages the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown in a variety of animal models that the resulting MVA was significantly virulent (Mayr, A. & Danner, K. [1978] Dev. Biol. Stand. 41: 225-34).

According to the present invention any MVA strain may be used. In a preferred embodiment, the MVA is characterized by having at least one, two, or preferably three of the following advantageous properties:
   (i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa;
   (ii) failure to replicate in a mouse model that is incapable of producing mature B and T cells and as such is severely immune compromised and highly susceptible to a replicating virus; and
   (iii) induction of at least the same level of specific immune response in vaccinia virus prime/vaccinia virus boost regimes when compared to DNA-prime/vaccinia virus boost regimes Examples for MVA virus strains used according to the present invention and deposited in compliance with the requirements of the Budapest Treaty are strains MVA 572 and MVA 575 deposited at the European Collection of Animal Cell Cultures (ECACC), Salisbury (UK) with the deposition numbers ECACC V94012707 and ECACC V00120707, respectively. In a preferred embodiment, said MVA is an MVA Vaccinia virus as deposited at the European Collection of Cell Cultures (ECACC) Salisbury (UK) under number V00083008 and derivatives thereof, also denoted "MVA-BN".

In one embodiment, the poxvirus according to the present invention comprises at least one heterologous nucleic acid sequence. The term "heterologous" is used hereinafter for any combination of nucleic acid sequences that is not normally found intimately associated with the virus in nature, such virus is also called "recombinant virus". Preferably, the heterologous nucleic acid sequence is a sequence coding for at least one antigen, antigenic epitope, and/or a therapeutic compound. The antigenic epitopes and/or the antigens can be antigenic epitopes and/or antigens of an infectious agent. The infectious agents can be viruses, fungi, pathogenic unicellular eukaryotic or prokaryotic organisms, and parasitic organisms. The viruses can be selected from the family of Influenza virus, Flavivirus, Paramyxovirus, Hepatitis virus, Human immunodeficiency virus, or from viruses causing hemorrhagic fever. The infectious agent can be bacillus anthracis.

According to still a further embodiment, but also in addition to the above-mentioned selection of antigenic epitopes, the heterologous sequences can be selected from another poxviral or a vaccinia source. These viral sequences can be used to modify the host spectrum or the immunogenicity of the virus.

In a further embodiment the poxvirus according to the present invention may code for a heterologous gene/nucleic acid expressing a therapeutic compound. A "therapeutic compound" encoded by the heterologous nucleic acid in the virus can be, e. g., a therapeutic nucleic acid such as an antisense nucleic acid or a peptide or protein with desired biological activity.

According to a further preferred embodiment the expression of heterologous nucleic acid sequence is preferably, but not exclusively, under the transcriptional control of a poxvirus promoter, more preferably of a vaccinia virus promoter.

According to still a further embodiment the insertion of heterologous nucleic acid sequence is preferably into a non-essential region of the virus genome as, for example, into a host range gene and/or at a naturally occurring deletion site (disclosed in PCT/EP96/02926) of the poxvirus genome. In another preferred embodiment of the invention, the heterologous nucleic acid sequence is inserted at or into an intergenic region of the poxviral genome (disclosed in PCT/EP03/05045). Methods how to insert heterologous sequences into the poxviral genome are known to a person skilled in the art.

According to a further embodiment the invention concerns the recombinant poxvirus according to the present invention for use as vaccine or medicament. Preferably, said vaccine or medicament does not include an additional growth factor that is already known to induce DC development, as FL and/or GM-CSF. The invention also relates to the recombinant poxvirus comprising a nucleic acid sequence coding for M-CSF as described herein for the treatment of proliferative diseases and/or autoimmune diseases as specified hereinabove. Furthermore, the present invention also encompasses the use of the recombinant poxvirus comprising a nucleic acid sequence coding for M-CSF for the preparation of a pharmaceutical composition for the treatment of proliferative and/or autoimmune diseases.

In more general terms, the invention relates to a vaccine or pharmaceutical composition comprising a recombinant poxvirus according to the present invention. Methods are known to the person skilled in the art how the vaccine or pharmaceutical composition can be prepared and administered to the animal or human body. If the vector is a viral vector such as a poxvirus or vaccinia virus vector, in particular an MVA vector, it may also be administered to the animal or human body according to the knowledge of the person skilled in the art, e. g. by intra venous, intra muscular, intra nasal, intra dermal or subcutaneous administration.

The pharmaceutical composition or the vaccine may generally include one or more pharmaceutical acceptable and/or approved carriers, additives, antibiotics, preservatives, adjuvants, diluents and/or stabilizers in addition to the promoter, expression cassette or vector according to the present invention. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of pharmaceutical compositions or vaccines, the recombinant poxvirus according to the present invention, in particular a recombinant vaccinia virus such as recombinant MVA is converted into a physiologically acceptable form. For vaccinia viruses, in particular MVA this can be done based on the experience in the preparation of poxvirus vaccines used for vaccination against smallpox (as described by Stickl, H. et al. [1974] Dtsch. med. Wschr. 99, 2386-2392). For example, the purified virus is stored at −80 C with a titre of 5×10$^8$TCID50/ml formulated in about 10 mM Tris, 140 mM NaCl pH 7. 4. For the preparation of vaccine shots, e. g., $10^1$-$10^9$ particles of the recombinant virus according to the present invention are lyophilized in phosphate-buffered saline (PBS) in the presence of 2% peptone and 1% human albumin in an ampoule, preferably a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e. g. human serum albumin) suitable for in vivo administration. A typical virus containing formulation suitable for freeze-drying comprises 10 mM Tris-buffer, 140 mM NaCl, 18.9 g/l Dextran (MW 36000-40000), 45 g/) Sucrose, 0.108 g/l L-glutamic acid mono potassium salt monohydrate pH 7.4. The glass ampoule is then sealed and can be stored between 4° C. and room temperature for several months. However, as long as no need exists the ampoule is stored preferably at temperatures below −20° C.

For vaccination or therapy the lyophilisate or the freeze-dried product can be dissolved in 0.1 to 0.5 ml of an aqueous solution, preferably water, physiological saline or Tris buffer, and administered either systemically or locally, i. e. by parenteral, intramuscular or any other path of administration know to the skilled practitioner. The mode of administration, the dose and the number of administrations can be optimized by those skilled in the art in a known manner.

In a further embodiment, the invention relates to the use of the recombinant poxvirus or the pharmaceutical composition according to the present invention for the generation of dendritic cells (DCs) from hematopoietic precursor cells, preferably in the manner as described herein above.

The invention also encompasses kits for inducing an immune response to an antigen in an animal. In an embodiment of the invention, the kit comprises a recombinant virus according to the invention and the antigen against which the immune response is to be induced. The virus may be a recombinant poxvirus, preferably a recombinant Vaccinia virus, in particular a recombinant MVA containing additional nucleotide sequences which are heterologous to the virus. In a preferred embodiment, the recombinant poxvirus is an MVA virus comprising a nucleic acid coding for M-CSF. Preferably, the viral genome does not include the sequence of further growth factors known to induce DCs, in particular not the sequence of FL and/or GM-CSF. In a particularly preferred embodiment, the kit comprises a recombinant poxvirus according to the present invention comprising a gene encoding M-CSF in a first vial/container and an antigen as described hereinabove in a second vial/container. The kit also comprises instructions to administer, in a first step, the first vial comprising the recombinant poxvirus according to the present invention to an animal in order to increase and/or generate dendritic cells (DCs) in said animal. The first vial may also be administered in vitro and/or ex vivo to hematopoietic precursor cells that have been removed from the animal. Methods to determine whether dendritic cells have been increased and/or generated after addition of M-CSF are extensively described herein. After said dendritic cells have been generated, the second vial comprising an antigen may be administered to the generated dendritic cells in vitro and/or ex vivo. Said exposed dendritic cells may then be reintroduced into the animal. Alternatively, the second vial comprising an antigen may be administered to the animal in vivo.

The detailed examples which follow are intended to contribute to a better understanding of the present invention. However, the invention is not limited by the examples. Other embodiments of the invention will be apparent to those skilled in the art from consideration of the specification and practice of the invention disclosed herein.

Example 1

Materials and Methods

Mice—C57BL/6 mice were obtained from Harlan Winkelmann (Borchen, Germany) and used at 6-10 weeks of age. FLKO mice were developed as described (14) and bred at the Institute of Labortierkunde (University of Zurich). Mice expressing green fluorescent protein (GFP) under the ubiquitin promoter [C57BL/6-Tg(UBC-GFP)30Scha/J, referred to hereafter as UBC-GFP mice] were purchased from Charles River Laboratories (Sulzfeld, Germany). Animal experiments were carried out with approval and under the guidelines of the local government animal ethics authorities.

Antibodies and Reagents—Recombinant (rec) flag-tagged murine (mu) FL was expressed in CHO cells and purified in house as previously described (10). recmuM-CSF and rechuM-CSF were obtained from Tebu-Bio (Frankfurt, Germany) and rechuM-CSF from R&D Systems (Wiesbaden, Germany). The cFMS Receptor Tyrosine Kinase Inhibitor (Cat. No. 344036) was obtained from EMD Biosciences (Darmstadt, Germany). Oligonucleotides containing CpG motifs (CpG2216 and CpG1668) were synthesized by TIB MOLBIOL (Berlin, Germany) according to published sequences (35). lmiquimod (R837) and palmitoyl-3-cysteine-serine-lysine-4 (Pam-3-Cys) were purchased from InvivoGen (San Diego, USA). Poly(cytidylic-inosinic) acid (poly I:C)), lipopolysaccharide (LPS) and 7-Allyl-7,8-dihydro-8-oxoguanosine (Loxoribine) were purchased from Sigma-Aldrich (Taufkirchen, Germany). All antibodies, unless otherwise stated, were obtained from Becton Dickinson, Germany, with the following exceptions: purified and FITC-conjugated anti-CD11c (rat clone 223H7) and anti-Ly49Q (Biozol Diagnostica Vertrieb GmbH, Eching, Germany), anti-mPDCA-1 (Miltenyi Biotec, Bergisch Gladbach, Germany) and anti-F4/80 (NatuTec GmbH, Frankfurt, Ger), anti-CD117-PeCy7 (clone 2B8), anti-CD34-Pe (clone RAM34) (NatuTec GmbH, Frankfurt, Germany) and anti-CD115 (clone AFS98, and an isotype matched Rat IgG2a control). It should be noted that another M-CSR mAb (clone 604B5 2E11, Serotec GmbH, Dusseldorf, Germany) was also used but staining with this mAb, unlike with clone AFS98, was extremely low on total BM and M-CSFR expression was undetectable on CLP using this clone . . . many Hybridomas, the supernatants of which were used in the depletion cocktail for ex vivo DC purification (21), were provided by Professor Ken Shortman, WEHI, Melbourne, Australia.

M-CSF and FL BM cultures—BM cells were flushed from femurs and tibiae of mice. Red cell lysis buffer (Sigma-Aldrich) was used to deplete red blood cells from the BM cell suspensions. BM cells were then either cultured directly or after depletion. To deplete, BM cells were incubated for 30 min with rat antibodies to CD11c and CD45R (B220) followed by 30 min incubation with goat anti-rat magnetic beads (Qiagen, Hilden, Germany). The depletion procedure routinely removed 65-80% of total BM cells. It should be noted that depletion with the beads only, in the absence of the rat antibodies, also depleted about 50% of the BM cells, presumably via FcR/Ig interactions. Total BM cells or depleted BM cells were cultured at $1.5 \times 10^6$ cells/ml in RPMI-1640 media (Gibco) supplemented with 10% FCS, 50 μM beta-mercaptoethanol, 100 IU/ml penicillin/streptomycin (complete media) and either 20 ng/ml recmuM-CSF or rechu-MCSF or 35 ng/ml recmuFL for 6-8 days at 37° C. in a humidified atmosphere containing 5% $CO_2$. The M-CSF cultures were fed with fresh M-CSF every 3 days, without media change.

Surface staining of M-CSF or FL BM cultures—Harvested cells were washed in PBS containing 2% FCS and 2 mM EDTA (FACS buffer). FcR binding was then blocked by incubation with 1 mg/ml purified anti CD16/32 monoclonal antibody (clone 2.4G2) for 20 mins on ice. An equal volume of 2× concentrated specific antibody stain was then added to the cell suspension and incubated for a further 20 mins. Cells were washed in FACS buffer and resuspended in FACS buffer containing 1 μg/ml propidium iodide.

Activation of DC subsets and analysis of cytokine production by ELISA—Unsorted M-CSF or FL BM cultures or sorted DCs ($0.25–0.5 \times 10^6$ cells/ml) were stimulated for 18-24 hrs in complete media with or without an added stimulus. The stimuli used were as follows: 1 μg/ml Pam-3-Cys, 100 μg/ml poly(I:C), 1 μg/ml LPS, 1 μg/ml R837, 1 mM Loxoribine, 0.5 μM CpG2216, 0.5 μM CpG1668. Culture supernatants were assayed for the presence of IFN-α by two-site ELISA as previously described (21). Other cytokines (IL-12 p70, IL-6, TNF-α, MCP-1 and IFN-γ) were measured using the Cytometric Bead Array, Mouse Inflammation Kit (Becton Dickinson). Stimulated DCs were blocked as stated above and stained with antibodies directed to CD8a, CD40, CD69, CD80 and CD86.

In vivo M-CSF treatment—Wild type and FLKO mice were treated ip with 10 μg of M-CSF in 0.01% BSA (100 μl volume), or with vehicle alone, for five consecutive days. At the end of five days mice were sacrificed. The peritoneum was flushed 3 times with Complete media and then organs were collected for DC purification.

Ex vivo DC purification—DCs were purified from spleens of M-CSF or vehicle treated mice essentially as previously described (21), using FACS buffer, RPMI and 1.077A Nycodenz (Progen Biotechnik GmbH, Heidelberg, Germany) that was adjusted to mouse osmolarity (308 mOsm).

Culturing of Progenitor Cells.

CMP (Lin$^-$Sca-1$^-$ckit$^+$CD34$^+$FcR$^{int}$), CLP (Lin$^-$Sca-1$^+$c-kit$^{int}$IL-7R$^+$Thy-1$^-$) or granulocyte/macrophage progenitors (GMP, Lin$^-$Sca-1$^-$c-kit$^+$CD34$^+$FcR$^{hi}$) were isolated from C57BL/6 BM as previously described[21] and sorted to greater than 95% purity on a FACS-ARIA instrument. 2500 cells and serial 2-fold dilutions thereof were added to a 1 ml suspension of UBC-GFP BM cells in a 24-well plate. Final UBC-GFP BM cell concentration was $1.0 \times 10^6$ cells/ml. M-CSF or FL cultures were carried out in these wells as described above. After 6 days, samples were enumerated, analysed by FACS, and progeny arising from the C57BL/6 progenitors were gated as GFP$^{neg}$ cells. To analyse M-CSFR (CD115) and Flt3 (CD135) expression on CLP (Lin$^-$Sca-1$^+$c-kit$^{int}$IL-7R$^+$Thy-1$^-$), lineage depleted cells were first stained with Sca-1-FITC and Thy-1-PE antibodies and the Sca-1$^+$Thy-1$^-$ cells were sorted. These pre-enriched cells (>95% purity when reanalysed) were then stained with CD117-PE-CY7, IL-7R-APC and either CD115-PE or CD135-PE.

Example 2

Total BM Cells Cultured with M-CSF are Potent Producers of IFN-α in Response to CpG-ODN Culture of mouse bone marrow (BM) cells with FL for 8-10 days has been reported to lead to the generation of millions of highly pure pDCs and cDCs that closely resemble the DC populations of steady state mouse spleen (19). To routinely test the kinetics of pDC development within these FL cultures, the IFN-α producing capacity of total BM cells incubated with FL in a multiwell format over a time course of 0-7 days was analyzed. A parallel culture of total BM cells with M-CSF was included as a negative control, because M-CSF is routinely used to generate macrophages from BM cells. Usually, the media and M-CSF are replaced every few days and only adherent cells are harvested at the end of a culture period of 7 days or longer (17). Instead, M-CSF cultures were treated exactly as the FL cultures, and wells of total M-CSF cultures (including adherent and non-adherent cells) were analyzed for IFN-α production in response to CpG-2216. Unexpectedly, IFN-α was induced to high levels in the M-CSF cultures. Moreover, the IFN-α produced in response to CpG-2216 increased with culture time, implying that IFN-α producing cells were being generated in the course of the M-CSF culture (FIG. 1A).

Example 3

The IFN-α Producers Induced in M-CSF BM Cultures Display Characteristics of pDC, but Develop without the Influence of FL Depletion of pDCs and cDCs from total BM cells depleted the CpG-induced IFN-α producing capacity of BM cells. When the DC-depleted BM cells were cultured with M-CSF for 6 days, potent IFN-α producing capacity was detected again in the non-adherent cells of the M-CSF culture.

To determine whether any of the non-adherent M-CSF-generated cells displayed the phenotype expected of a pDCs they were stained with CD11c and CD45RA. Indeed, a population of 10-20% of cells within the cultures expressed high levels of CD45RA and medium levels of CD11c, together with the lack of CD3, CD19 or CD49b or NK1.1 expression, low side scatter and forward scatter this was commensurate with the phenotype of pDCs (FIG. 1B and data not shown).

It was clear that M-CSF could drive pDC development yet the yield of pDCs was substantially less then that obtained with FL. When the two cultures were compared side by side after six days of culture, M-CSF was approximately 10-fold less efficient than FL (FIG. 1B). Day 6 was chosen for comparison because after this stage the M-CSF cultures become very acidic and sorted DC populations from the cultures died much more rapidly in culture and failed to produce cytokines.

To determine if M-CSF induction of pDCs requires endogenous FL, replicate BM cultures were studied from mice in which the FL gene had been ablated (FLKO mice). Total cell numbers obtained from the BM cultures of FLKO mice were reduced whether cultures were conducted with M-CSF addition or FL addition (FIG. 1C), indicating that pDCs developed even in the absence of FL. It was clear that cells with the phenotype and morphology of pDCs were produced by culture of BM first depleted of any DC populations and in the presence of only exogenous M-CSF, without the potential influence of any FL. These M-CSF generated pDCs are referred to as M-pDC.

Example 4

Detailed Surface Phenotype of M-pDC

Figure 2:
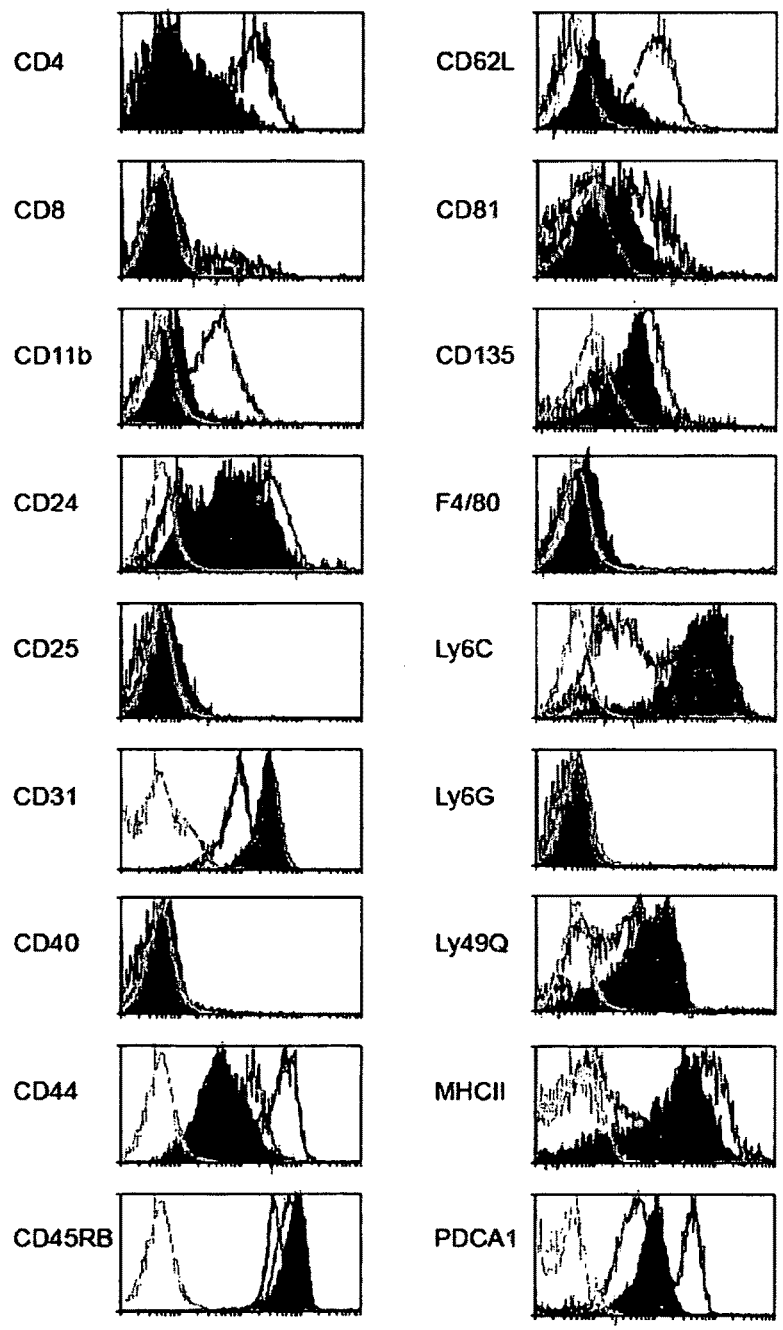
FIG. 2. Surface phenotype of M-pDC compared to FL-pDC and ex-vivo isolated spleen pDC. Stained cells from day 6 M-CSF cultures (filled histograms), FL cultures (grey open histograms) or freshly isolated spleen DC (black histograms) were gated on pDC by selecting for the expression of CD11c and CD45RA or CD45R amongst the PI negative cells. The expression of a range of surface markers on the pDC surface is shown. The light grey histograms represent the background staining of the M-pDC within each stain. All M-pDC also lacked expression of CD3, CD19, CD49b and NK1.1. The surface phenotypes shown are from one experiment representative of 2-5 experiments for M-pDC, 2-3 experiments for FL-pDC and 2 experiments for spleen pDC.

Extensive phenotyping of the M-pDCs from wild type and FLKO mice shows that the elicited pDCs displayed, an identical phenotype for over 40 surface markers. When compared to pDCs generated in vitro with FL (FL-pDC), numerous cell surface markers were different between the pDCs generated with the two different cytokines. In fact, as seen in FIG. 2, the M-pDCs displayed a phenotype that appeared for many markers to be intermediate between FL-pDC and ex-vivo isolated spleen pDC. Molecules that are recognized as differentiation markers of pDC; Ly49Q (20), CD4 (21) and MHCII, are all higher on M-pDCs than on FL-pDCs and are very similar to the levels on spleen pDCs. The M-pDCs express a similarly high level of Ly6C as the ex vivo spleen pDCs. Because it has recently been shown that pDC develop from Ly6C$^-$ precursors, M-pDCs represent a further differentiated state in pDC development than the FL-pDC (22).

The surface expression of B7H1, CD81, CD62L and CD11b on the M-pDCs also more closely resemble the ex-vivo pDCs than the FL-pDC.s. In contrast, M-pDCs express the lowest levels of CD44 and a spread of surface CD24 bridging the high levels expressed by spleen pDCs and the low levels expressed by FL-pDCs. Also, M-pDCs express low levels of F4/80. The low F4/80 expression lends a "myeloid" phenotype to the M-pDCs. M-pDCs express very low levels of CD11b (in the order of 10-fold lower than FL-pDC) and do not express Ly6G.

Example 5

Highly purified M-pDCs are activated by ligands for TLR7 and TLR9

Similar to FL-pDC and ex-vivo pDC, the M-pDC were not activated with ligands to TLR3, TLR4 or GM-CSF but showed a very minor surface activation to the TLR2 ligand Pam-3-Cys (FIG. 3A). The survival of the M-pDC to these stimuli was extremely poor (<5%), data not shown.

Similar to FL-pDCs and ex-vivo pDCs, sorted M-pDC were activated with ligands for TLR7 and 9, as indicated by elevated expression of CD8a, CD69, CD86 and CD40 (FIG. 3B and data not shown). M-pDC only produced detectable cytokines to TLR7 and 9 ligands (FIG. 3C and data not shown). In response to a type A CpG-ODN (CpG2216) M-pDCs produced high levels of IFN-α (FIG. 3C). The absolute amount of IFN-α produced by the M-pDC was in the range of 2-fold less that produced by FL-pDC. Other cytokines induced by TLR 7 and 9 ligands included IL-6 and TNF-α (FIG. 3D). The M-pDC produced similar levels of IL-6 as the FL-pDC but they produced higher levels of TNF-α than the FL-pDC. The production of IL-10, IL-12p70, MCP-1 and IFN-γ by the M-pDC was also tested but none of these cytokines were detected.

After overnight stimulation the M-pDCs were examined for changes in phenotype. The M-pDCs, similarly to FL-pDCs and ex-vivo pDCs, expressed elevated levels of CD8a, CD69, CD86 and CD40 upon TLR stimulation.

Example 6

Conventional DCs also Develop in M-CSF BM Cultures

Figure 1:
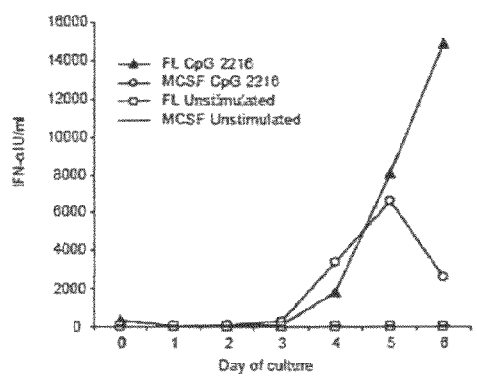
FIG. 1. M-CSF drives pDC and cDC development from BM cells, even in the absence of FL. A. Replicate wells of C57BL/6 BM cells depleted of B220+ and CD11c+ cells were incubated for 6 days with M-CSF (20 ng/ml) added at day 0 and again at day 3 or with FL (35 ng/ml) added at day 0 only. On each of days 0-6, separate wells were stimulated O/N with CpG-2216 or left unstimulated and the supernatants were assayed for IFN-α. B. C57BL/6 BM cells depleted of B220+ and CD11c+ cells were incubated for 6 days with M-CSF (20 ng/ml) added at day 0 and again at day 3. On day 6 the cells were harvested and stained with antibodies to detect CD11c and CD45RA expression. Cells with the phenotype of pDC and cDC populations are shown boxed in the left panel. The number of cells in each of the pDC and cDC populations are shown in the right panel and compared to numbers obtained from day 6 FL-generated DC or media only also using BM cells depleted of B220+ and CD11c+ cells. C. BM cells from mice lacking FL were similarly depleted of B220+ and CD11c+ cells and incubated in replicate wells for 0-6 days with FL, M-CSF (with additional feeding at day 3). On each of days 0-6, separate wells were stimulated O/N with CpG-2216 or left unstimulated and the supernatants were assayed for IFN-α (left panel). The pDC and cDC populations present at day 6 in the FLKO cultures are shown in right panel. Data shown are from one experiment representative of 3 similar experiments for the multiple timepoints (A) one experiment that was carried out for the multiple timepoints and 3 additional experiments for day 6 and 0 timepoints (C, left panel), one experiment representative of 3 experiments of day 6 FL cultures and more than 5 experiments of day 6 M-CSF cultures (B) and one experiment that is representative of 4 experiments (C, right panel). In media only control cultures of B & C (right panels) no M-DC were detectable.
Figure 1:
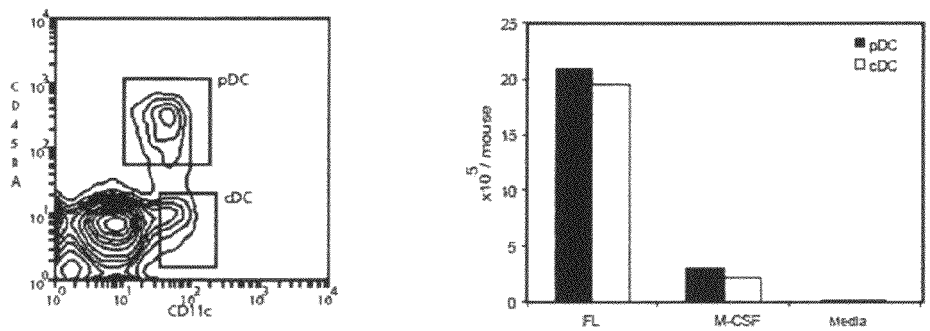
Figure 1:
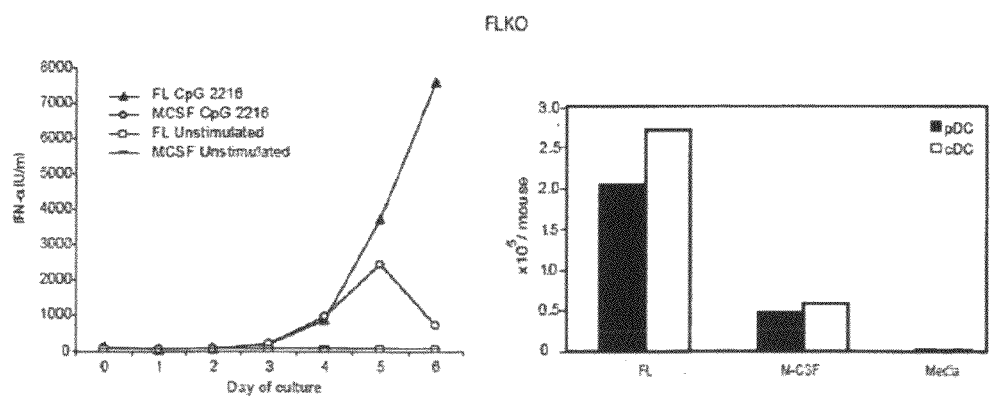

As shown in FIG. 1, CD11c$^+$ cells that did not concomitantly express CD45RA or T, B or NK cell markers were also induced in the M-CSF BM cultures. Like the pDCs, these cells also developed in BM cultures of FLKO mice. Surface phenotype analyses of these cells reveals that they resemble conventional (c) DC, expressing costimulation markers and MHCII (FIG. 7). The M-cDC generated within the M-CSF BM cultures, like the FL-cDC were heterogeneous with respect to activation markers (CD80, CD86, CD40, MHCII) but overall displayed higher levels of these markers than the cDC induced in FL cultures. In the FL-DC cultures CD11b$^{lo}$CD24$^{hi}$ cDC correspond to the CD8$^+$CD11b$^-$CD24$^{hi}$CD205$^+$ splenic cDC equivalents. The cDC generated in the M-CSF cultures contain cells expressing a lower level of CD11b but they lack the very high CD24 expressing cells present amongst FL-cDC, suggesting that perhaps they do not produce CD8$^+$ cDC equivalents. Upon TLR stimulation the cDC were activated to resemble mature, ex-vivo activated cDCs.

Of interest in the activation of the M-cDCs and M-pDCs is that they respond well to TLR9 ligands. This is quite a different scenario from macrophages within M-CSF cultures that downregulate TLR9 and consequently respond poorly to TLR9 ligands (23).

Example 7

M-pDC Generation is Dependent Upon Active c-fms

It has previously been shown that Flt3+ cells within the BM common myeloid progenitors (CMP) and common lymphoid progenitors (CLP) are the precursors of cDCs and pDCs within mouse lymphoid organs (24,25) and it has been assumed that FL is essential for DC development. Thus the generation of DCs, particularly the generation of pDCs with a typical monocytic protein, in the absence of FL, was unexpected. As shown in FIG. 1 the M-pDCs clearly develop in the absence of FL, yet they also show many similarities to FL-pDCs. Given that M-CSF and FL, as well as their respective receptors, Flt3 and c-fms, have structural similarities, whether M-CSF was signalling through Flt3 was investigated. That is, whether M-CSF would act as a FL surrogate that also signalled via Flt3, generating M-CSF-induced "FL-DCs" was examined.

Figure 8:
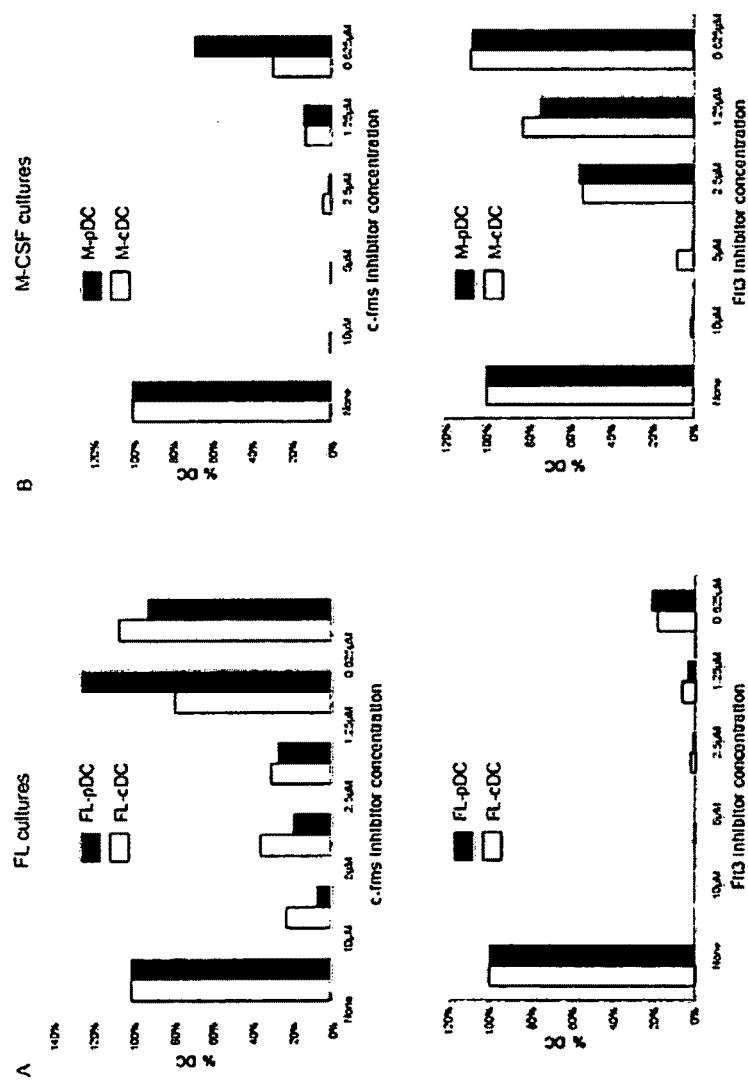

There are numerous inhibitors of receptor tyrosine kinases, with varying levels of cross-reactivity. The inhibitor cFMS Receptor Tyrosine Kinase Inhibitor (Calbiochem), which is reported to be a highly specific c-fms inhibitor, was used. Indeed, cFMS Receptor Tyrosine Kinase Inhibitor entirely blocked the haematopoietic effects of M-CSF over a broad concentration range (FIG. 6). The highest concentrations of inhibitor also blocked the generation of DCs by FL. However, cFMS inhibitor used in the range of 0.63-1.3 µM had only minor effects on FL-mediated FL-DC generation (FIG. 4A and FIG. 8). Since these same low concentrations still blocked M-DC generation, M-pDC generation does not involve M-CSF acting through the Flt3 receptor tyrosine kinase. Although the c-fms inhibitor is likely a promiscuous receptor tyrosine kinase inhibitor at high concentrations, at low concentrations it did not inhibit FL-DC generation, demonstrating that it is, indeed, c-fms specific. In stark contrast, a Flt3 inhibitor (Flt3 Inhibitor II, Calbiochem) was highly inhibitory for generation of FL-DC but not M-DC (FIG. 4B and FIG. 8). Thus, M-pDCs and M-cDCs can be generated by M-CSF via c-FMS signalling, independently of Flt3 and FL in vitro.

Example 8

M-CSF Induces M-pDC and M-cDC Generation in Vivo

Recently it has been reported that op/op mice that carry a mutation in the gene for M-CSF and thus lack functional M-CSF, exhibit reduced numbers of splenic DC[27]. Specifically cDC were reduced about 2-fold and pDC about 3-fold. This was substantially less of an effect than that seen in mice lacking FL but nevertheless, lack of M-CSF did result in reduced DC numbers, further substantiating the assumption that M-CSF is a DC poietin. To further validate the studies initiated by MacDonald et al (2005), M-CSF was administered to mice in order to analyze whether M-CSF could actually increase DC numbers in vivo. According to other references in the prior art, a range of exogenous M-CSF concentrations in the range of 10 to 200 µg/day has been administered. The source of M-CSF used has varied widely and consequently, as well as the specific activity. It is thus impossible to gauge an optimal or saturating level of M-CSF to administer. Moreover, it has been reported that M-CSF has an extremely short half-life of only 10 mins in the circulation[28]. Due to the prohibitive cost of commercial M-CSF with a determined specific activity a 'proof of principal' trial experiment was conducted and 10 µg/day of M-CSF to C57BL/6 or FLKO mice for 5 days were administered. This amount was neither titrated nor was it attempted to extend the application period. It was clear however that after the 5 day application period a huge increase in F4/80$^{hi}$ cells was observed in peritoneal lavages of the mice that we examined (data not shown). Said observations indicate that M-CSF indeed was inducing an effect in vivo.

Analysis of DC populations in the spleen revealed that M-CSF was inducing a reproducible increase of about 2-fold in both pDC and cDC numbers. This increase was evident in C57BL/6 and FLKO mice (FIG. 5). A closer examination of cDC subpopulations indicated that CD8+ and CD8-populations were increased fairly uniformly (data not shown). The M-CSF treatment did not induce an increase in total splenocytes (FIG. 5B) although as evident in FIG. 5A, there was an increase in light density, non-DC, purified after M-CSF treatment. The CD11cintCD45RA- and CD45RAhiCD11c-/lo cells could potentially contain immature DC populations but this was not examined further. A more extensive increase (greater than 6-fold) of cells that resembled DC was also evident in the peritoneal lavage of a C57BL/6 mouse examined (data not shown).

This is the first evidence that as well as inducing pDC and cDC in vitro, M-CSF is also capable of increasing DC numbers in vivo, even in the absence of FL.

Example 9

Progenitor Cell Populations that Harbour M-DC Precursor Potential

The identification of DC subtypes that could be generated in the absence of FL both in vivo and in vitro immediately raises the question of the nature of their precursor cells. It has been considered whether this factor acts on an early lineage progenitor or, since M-CSF is traditionally considered a 'myeloid' growth factor, on a later precursor within the myeloid lineage to generate M-DC. CMP, GMP and CLP were purified from mouse BM. Serial dilutions of the purified cell populations were admixed with 'feeder' UBC-GFP BM cells and M-CSF cultures were carried out for 6 days.

Analyses of the progeny of each of the 3 precursor populations revealed that committed GMP were not capable of M-DC production in said culture conditions (FIGS. 6B and 6C). CMP were quite efficient precursors of M-cDC, producing an output of 8-10 M-cDC per input progenitor cell but this level dramatically dropped off with input cell numbers lower than 156, possibly suggesting that the M-cDC were arising from a small subpopulation of the CMP. The CLP on the other hand were at least 10-fold more efficient than CMP at M-pDC generation. The CLP produced an output of at least 10 M-pDC and about 5 M-cDC per input progenitor cell (FIGS. 6B and 6C). These data indicate that both CMP and CLP are progenitors that can respond to M-CSF to generate M-DC. Surprisingly the CLP were the most efficient M-pDC progenitors. We stained CLP with antibodies to M-CSFR (CD115, FIG. 6D). About 20% of cells within the CLP gate expressed high levels of CD115. Flt3 (CD135) staining done in parallel showed that the majority of the CLP were CD135+ and thus at least some of the CD115+ cells must also be CD135+. Moreover, many of the CLP expressed very low staining of CD115, just above the background of an isotype-matched control, indicating that indeed many CLP are armed with the necessary receptor to respond to M-CSF in the DC cultures described herein.

Thus the M-DC described herein most likely arise in vitro and in vivo from precursors within the CLP and CMP progenitor populations.

REFERENCES

The following references are cited herein. The entire disclosure of each reference is relied upon and incorporated by reference herein.

1. Steinman, R. M. and K. Inaba. 1999. Myeloid dendritic cells. *J Leukoc. Biol.* 66:205-208.
2. Shortman, K. and Y. J. Liu. 2002. Mouse and human dendritic cell subtypes. *Nat. Rev. Immunol.* 2:151-161.
3. Scheicher, C., M. Mehlig, R. Zecher, and K. Reske. 1992. Dendritic cells from mouse bone marrow: in vitro differentiation using low doses of recombinant granulocyte-macrophage colony-stimulating factor. *J Immunol Methods* 154:253-264.
4. Inaba, K., M. Inaba, N. Romani, H. Aya, M. Deguchi, S. Ikehara, S. Muramatsu, and R. M. Steinman. 1992. Generation of large numbers of dendritic cells from mouse bone marrow cultures supplemented with granulocyte/macrophage colony-stimulating factor. *J Exp. Med.* 176:1693-1702.
5. Sallusto, F. and A. Lanzavecchia. 1994. Efficient presentation of soluble antigen by cultured human dendritic cells is maintained by granulocyte/macrophage colony-stimulating factor plus interleukin 4 and downregulated by tumor necrosis factor alpha. *J Exp. Med.* 179:1109-1118.
6. Vremec, D., G. J. Lieschke, A. R. Dunn, L. Robb, D. Metcalf, and K. Shortman. 1997. The influence of granulocyte/macrophage colony-stimulating factor on dendritic cell levels in mouse lymphoid organs. *Eur. J. Immunol.* 27:40-44.
7. Gilliet, M., A. Boonstra, C. Paturel, S. Antonenko, X. L. Xu, G. Trinchieri, A. O'Garra, and Y. J. Liu. 2002. The development of murine plasmacytoid dendritic cell precursors is differentially regulated by FLT3-ligand and granulocyte/macrophage colony-stimulating factor. *J. Exp. Med* 195:953-958.
8. Brasel, K., S. T. De, J. L. Smith, and C. R. Maliszewski. 2000. Generation of murine dendritic cells from flt3-ligand-supplemented bone marrow cultures. *Blood* 96:3029-3039.
9. Brawand, P., D. R. Fitzpatrick, B. W. Greenfield, K. Brasel, C. R. Maliszewski, and T. De Smedt. 2002. Murine plasmacytoid pre-dendritic cells generated from Flt3 ligand-supplemented bone marrow cultures are immature APCs. *J. Immunol.* 169:6711-6719.
10. O'Keeffe, M., H. Hochrein, D. Vremec, J. Pooley, R. Evans, S. Woulfe, and K. Shortman. 2002. Effects of administration of progenipoietin 1, Flt-3 ligand, granulocyte colony-stimulating factor, and pegylated granulocyte-macrophage colony-stimulating factor on dendritic cell subsets in mice. *Blood* 99:2122-2130.
11. Pulendran, B., J. Banchereau, S. Burkeholder, E. Kraus, E. Guinet, C. Chalouni, D. Caron, C. Maliszewski, J. Davoust, J. Fay, and K. Palucka. 2000. Flt3-ligand and granulocyte colony-stimulating factor mobilize distinct human dendritic cell subsets in vivo. *J. Immunol.* 165:566-572.
12. Maraskovsky, E., K. Brasel, M. Teepe, E. R. Roux, S. D. Lyman, K. Shortman, and H. J. McKenna. 1996. Dramatic increase in the numbers of functionally mature dendritic cells in Flt3 ligand-treated mice: multiple dendritic cell subpopulations identified. *J. Exp. Med* 184:1953-1962.

13. Bjorck, P. 2001. Isolation and characterization of plasmacytoid dendritic cells from Flt3 ligand and granulocyte-macrophage colony-stimulating factor-treated mice. *Blood* 98:3520-3526.
14. McKenna, H. J., K. L. Stocking, R. E. Miller, K. Brasel, S. T. De, E. Maraskovsky, C. R. Maliszewski, D. H. Lynch, J. Smith, B. Pulendran, E. R. Roux, M. Teepe, S. D. Lyman, and J. J. Peschon. 2000. Mice lacking flt3 ligand have deficient hematopoiesis affecting hematopoietic progenitor cells, dendritic cells, and natural killer cells. *Blood* 95:3489-3497.
15. Ishii, K. J. and S. Akira. 2006. Innate immune recognition of, and regulation by, DNA. *Trends Immunol* 27:525-532.
16. Diebold, S. S., M. Montoya, H. Unger, L. Alexopoulou, P. Roy, L. E. Haswell, A. Al Shamkhani, R. Flavell, P. Borrow, and Reis e Sousa. 2003. Viral infection switches non-plasmacytoid dendritic cells into high interferon producers. *Nature* 424:324-328.
17. Hochrein, H., B. Schlatter, M. O'Keeffe, C. Wagner, F. Schmitz, M. Schiemann, S. Bauer, M. Suter, and H. Wagner. 2004. Herpes simplex virus type-1 induces IFN-alpha production via Toll-like receptor 9-dependent and—independent pathways. *Proc. Natl. Acad. Sci. U. S. A* 101:11416-11421.
18. Krug, A., S. Rothenfusser, V. Hornung, B. Jahrsdorfer, S. Blackwell, Z. K. Ballas, S. Endres, A. M. Krieg, and G. Hartmann. 2001. Identification of CpG oligonucleotide sequences with high induction of IFN-alpha/beta in plasmacytoid dendritic cells. *Eur. J. Immunol.* 31:2154-2163.
19. Naik, S. H., A. I. Proietto, N. S. Wilson, A. Dakic, P. Schnorrer, M. Fuchsberger, M. H. Lahoud, M. O'Keeffe, Q. X. Shao, W. F. Chen, J. A. Villadangos, K. Shortman, and L. Wu. 2005. Cutting edge: generation of splenic CD8+ and CD8– dendritic cell equivalents in Fms-like tyrosine kinase 3 ligand bone marrow cultures. *J. Immunol.* 174:6592-6597.
20. Omatsu, Y., T. Iyoda, Y. Kimura, A. Maki, M. Ishimori, N. Toyama-Sorimachi, and K. Inaba. 2005. Development of Murine Plasmacytoid Dendritic Cells Defined by Increased Expression of an Inhibitory NK Receptor, Ly49Q. *J Immunol* 174:6657-6662.
21. O'Keeffe, M., H. Hochrein, D. Vremec, I. Caminschi, J. L. Miller, E. M. Anders, L. Wu, M. H. Lahoud, S. Henri, B. Scott, P. Hertzog, L. Tatarczuch, and K. Shortman. 2002. Mouse plasmacytoid cells: long-lived cells, heterogeneous in surface phenotype and function, that differentiate into CD8(+) dendritic cells only after microbial stimulus. *J. Exp. Med* 196:1307-1319.
22. Kreisel, F. H., A. Blasius, D. Kreisel, M. Colonna, and M. Cella. 2006. Interferon-producing cells develop from murine CD31(high)/Ly6C(–) marrow progenitors. *Cell Immunol* 242:91-98.
23. Sweet, M. J., C. C. Campbell, D. P. Sester, D. Xu, R. C. McDonald, K. J. Stacey, D. A. Hume, and F. Y. Liew. 2002. Colony-stimulating factor-1 suppresses responses to CpG DNA and expression of toll-like receptor 9 but enhances responses to lipopolysaccharide in murine macrophages. *J Immunol* 168:392-399.
24. D'Amico, A. and L. Wu. 2003. The early progenitors of mouse dendritic cells and plasmacytoid predendritic cells are within the bone marrow hemopoietic precursors expressing Flt3. *J. Exp. Med* 198:293-303.
25. Karsunky, H., M. Merad, A. Cozzio, I. L. Weissman, and M. G. Manz. 2003. Flt3 ligand regulates dendritic cell development from Flt3+ lymphoid and myeloid-committed progenitors to Flt3+ dendritic cells in vivo. *J Exp. Med.* 198:305-313.
26. MacDonald, K. P., V. Rowe, A. D. Clouston, J. K. Welply, R. D. Kuns, J. L. Ferrara, R. Thomas, and G. R. Hill. 2005. Cytokine expanded myeloid precursors function as regulatory antigen-presenting cells and promote tolerance through IL-10-producing regulatory T cells. *J. Immunol.* 174:1841-1850.
27. Bartocci, A., D. S. Mastrogiannis, G. Migliorati, R. J. Stockert, A. W. Wolkoff, and E. R. Stanley. 1987. Macrophages specifically regulate the concentration of their own growth factor in the circulation. *Proc. Natl. Acad. Sci. U. S. A* 84:6179-6183.
28. Rolland, A., L. Guyon, M. Gill, Y. H. Cai, J. Banchereau, K. McClain, and A. K. Palucka. 2005. Increased blood myeloid dendritic cells and dendritic cell-poietins in Langerhans cell histiocytosis. *J Immunol* 174:3067-3071.
29. Guha-Thakurta, N. and J. A. Majde. 1997. Early induction of proinflammatory cytokine and type I interferon mRNAs following Newcastle disease virus, poly [rl:rC], or low-dose LPS challenge of the mouse 1. *J Interferon Cytokine Res.* 17:197-204.
30. Vollstedt, S., M. O'Keeffe, B. Ryf, B. Glanzmann, H. Hochrein, and M. Suter. 2006. The long-term but not the short-term antiviral effect of IFN-alpha depends on Flt3 ligand and pDC. *Eur. J. Immunol.* 36:1231-1240.
31. Franch ini, M., H. Hefti, S. Vollstedt, B. Glanzmann, M. Riesen, M. Ackermann, P. Chaplin, K. Shortman, and M. Suter. 2004. Dendritic cells from mice neonatally vaccinated with modified vaccinia virus Ankara transfer resistance against herpes simplex virus type I to naive one-week-old mice. *J. Immunol.* 172:6304-6312.
32. Itoh, Y., T. Okanoue, S. Sakamoto, K. Nishioji, and K. Kashima. 1997. The effects of prednisolone and interferons on serum macrophage colony stimulating factor concentrations in chronic hepatitis B. *J Hepatol.* 26:244-252.
33. Gill, M. A., P. Blanco, E. Arce, V. Pascual, J. Banchereau, and A. K. Palucka. 2002. Blood dendritic cells and DC-poietins in systemic lupus erythematosus. *Hum. Immunol.* 63:1172-1180.
34. Chitu, V. and E. R. Stanley. 2006. Colony-stimulating factor-1 in immunity and inflammation. *Curr. Opin. Immunol* 18:39-48.
35. Spies, B., H. Hochrein, M. Vabulas, K. Huster, D. H. Busch, F. Schmitz, A. Heit, and H. Wagner. 2003. Vaccination with plasmid DNA activates dendritic cells via Toll-like receptor 9 (TLR9) but functions in TLR9-deficient mice. *J. Immunol.* 171:5908-5912.
36. Hsu et al. 1996. Vaccination of Patients with B-Cell Lymphoma Using Autologous Antigen-Pulsed Dendritic Cells. *Nat. Med.* 2:52-58.
37. Paglia, et al. 1996. Murine Dendritic Cells Loaded In Vitro with Soluble Protein Prime Cytotoxic T Lymphocytes against Tumor Antigen In Vivo. *J. Exp. Med.* 1996, 183: 317-22.
38. Christensen and Shlomochik. 2007. Regulation of lupus-related autoantibody production and clinical disease by Toll-like receptors. *Semin. Immunol.* 19: 11-23.
39. Sweet et al. 2002. Colony-stimulating factor-1 suppresses responses to CpG DNA and expression of toll-like receptor 9 but enhances responses to lipopolysaccharide in murine macrophages. *J. Immunol.* 168: 392-99.
40. Xu et al., 2004. translation: Detection of FLT3 gene and FLT3/ITD gene mutation in chronic myeloid leukemia and its significance. *Ai Zheng,* 23:1218-21 [abstract available in English].
40. Hubei, et al., 2002. Therepeutic use of cytokines to modulate phagocyte function for the treatment of infections diseases: Current status of Granulocyte Colony-Stimulating Factor, Granulocyte-Macrophage Colony-Stimulating Factor, Macrophage Colony-Stimulating Factor, and Interferon-γ. *J. Infect. Dis.,* 185: 1490-501.

41. Fogg et al., 2006. A Clonogenic Bone Marrow Progenitor Specific for Macrophages and Dendritic Cells. *Science*, 311:83-87.
42. Takashima et al., 1995. Colony-stimulating Factor-1 Secreted by Fibroblasts Promotes the Growth of Dendritic Cell Lines XS Series) Derived From Murine Epidermis. *J. Immunol.*, 154:5128-35.
43. Chito and Stanley, 2006. Colony-stimulating Factor-1 in Immunity and Inflammation. *Curr. Op. Immunol.*, 28:39-48.
44. U.S. Pat. No. 7,198,948.
45. Stoll M L, Price K D, Silvin C J, Jiang F, Gavalchin J. 2007. Immunization with peptides derived from the idiotypic region of lupus-associated autoantibodies delays the development of lupus nephritis in the (SWRxNZB)F(1) murine model. *J Autoimmun*. (Epub ahead of print)
46. Zhang W, Frank M B, Reichlin M. 2002. Production and characterization of human monoclonal anti-idiotype antibodies to anti-dsDNA antibodies. *Lupus*, 11(6):362-9.
47. Graf C, Heidel F, Tenzer S, Radsak M P, Solem F K, Britten C M, Huber C, Fischer T, Wolfel T. 2006. A neoepitope generated by a FLT3 internal tandem duplication (FLT3-ITD) is recognized by leukemia-reactive autologous CD8+ T cells. *Blood*. (Epub ahead of print).
48. Kappelmayer J, Udvardy M, Antal-Szalmas P. 2007. Pgp and FLT3: identification and modulation of two proteins that lead to chemotherapy resistance in acute myeloid leukemia. *Curr Med Chem.*, 14:519-30.
49. Zheng R, Small D. 2005. Mutant FLT3 signaling contributes to a block in myeloid differentiation. *Leuk Lymphoma*. 46:1679-87.
50. Advani A S. 2005. FLT3 and acute myelogenous leukemia: biology, clinical significance and therapeutic applications. *Curr Pharm Des*. 11:3449-57.
51. Kamps A W A, Hendriks D, Smit J W, Vellenga, E. 1999. Role of macrophage colony-stimulating factor in the differentiation and expansion of monocytes and dendritic cells from CD34+ progenitor cells. *Med Oncol*. 16:46-52.
52. Cremer I, Dieu-Nosjean M-C, Maréchal S, Dezutter-Dambuyant C, Goddard S, Adams D, Winter N, Menetrier-Caux C, Sautès-Fridman, C, Fridman W H, Mueller C G. 2002. Long-lived immature dendritic cells mediated by TRANCE-RANK interaction. *Blood*. 100(10):3646-3655.
53. Mollah Z U A, Aiba S, Nakagawa S, Hara M, Manome H, Mizuashi M, Ohtani T, Yoshino Y, Tagami H. 2003. Macrophage colony-stimulating factor in cooperation with transforming growth factor-β1 induces the differentiation of CD34+ hematopoietic progenitor cells into Langerhans cells under serum-free conditions without granulocyte-macrophage colony-stimulating factor. *J Invest Dermatol.* 120:256-265.
54. Briard D, Azzarone B, Brouty-Boyé D. Importance of stromal determinants in the generation of dendritic and natural killer cells in the human spleen. *Clin. Exp. Immunol.* 140:265-273.

The invention claimed is:

1. A method of Fms-like-Tyrosine-Kinase 3-Ligand-(FL)- and Granulocyte-Macrophage-Colony Stimulating Factor- (GM-CSF)-independent generation of dendritic cells (DCs) comprising:
   (a) culturing hematopoietic precursor cells;
   (b) administering Macrophage-Colony Stimulating Factor (M-CSF) to the precursor cells; and
   (c) quantitating the number of plasmacytoid dendritic cells (pDCs) by measuring the level of at least two cell surface markers that characterize the quantitated cells as pDCs; wherein the administration of M-CSF causes an FL-independent and GM-CSF-independent generation of pDCs from the hematopoietic precursor cells.

2. The method of claim 1, further comprising quantitating the number of conventional dendritic cells (cDCs).

3. The method of claim 2, wherein the numbers of cDCs are quantitated before and after administration of M-CSF and wherein the number of cDCs after M-CSF administration is increased over the number of cDCs before administration of M-CSF.

4. The method of claim 1, wherein the precursor cells are bone marrow cells.

5. The method of claim 1, wherein the numbers of pDCs are quantitated before and after administration of M-CSF and wherein the number of pDCs after M-CSF administration is increased over the number of pDCs before administration of M-CSF.

6. The method of claim 5, wherein at least one of the cell surface markers is selected from CD11c, CD45R, CD45RA, PDCA-1, CCR9, Ly49Q, Ly6C, Siglec-H, HLA-DR, CD4, CD123, BDCA-2, or BDCA-4.

7. The method of claim 3, wherein the number of cDCs is quantitated by measuring the level of at least one cell surface marker selected from CD11c, CD11b, CD4, CD8, Sirp-alpha, DEC-205, MHCII, 33D1, HLA-DR, BDCA-1, BDCA-3, or CLEC9A.

8. The method of claim 1, wherein the DCs are harvested.

9. The method of claim 1, wherein cytokines produced by the generated DCs are collected.

10. The method of claim 9, wherein the cytokine produced is selected from the group comprising IFN-α, IFN-β, IL-1, IL-6, IL-8, IL-10, IL-12, IL-15, IL-16, IL-18, IL-23, IL-27, IL-28, IL-29, TNF-α, TNF-β and chemokines.

11. The method of claim 10, wherein the cytokine produced is IFN-α.

12. The method of claim 1, further comprising exposing the DCs to an antigen.

13. The method of claim 12, wherein the antigen is derived from a tumor, a virus, bacteria, fungi, parasite, prion, plant, mollusc, arthropod, or from vertebrate toxins.

14. The method of claim 1, further comprising stimulating the DCs by exposing them to at least one stimulatory agent.

15. The method of claim 14, wherein the at least one stimulatory agent is IFN-α, IFN-β, IL-6, IL-10, IL-12, TNF-α, a TLR-agonist, virus, bacteria, fungi, plant or parts thereof.

16. The method of claim 1, wherein the M-CSF is administered in a virus vector.

17. The method according to claim 16, wherein the virus vector is a poxvirus vector.

18. The method of claim 17, wherein the poxvirus vector is a Vaccinia virus vector.

19. The method of claim 18, wherein the Vaccinia virus vector is a Modified Vaccinia virus Ankara (MVA) vector.

20. The method of claim 1, wherein the M-CSF is administered as a polypeptide or as a nucleic acid that is expressed in the cell.

21. The method of claim 20, wherein the nucleic acid is DNA or RNA.

* * * * *